(12) United States Patent
Monson et al.

(10) Patent No.: US 11,482,888 B2
(45) Date of Patent: Oct. 25, 2022

(54) ANTENNA FOR USE WITH RF ENERGY HARVESTING

(71) Applicant: Medtronic, Inc., Minneapolis, MN (US)

(72) Inventors: Robert J. Monson, St. Paul, MN (US); Andrew Thomas Fried, St. Paul, MN (US); Bruce T. Peacock, Lake Elmo, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 17/350,983

(22) Filed: Jun. 17, 2021

(65) Prior Publication Data

US 2021/0399584 A1    Dec. 23, 2021

Related U.S. Application Data

(60) Provisional application No. 63/041,665, filed on Jun. 19, 2020.

(51) Int. Cl.
*H02J 50/20*    (2016.01)
*H02J 50/27*    (2016.01)
(Continued)

(52) U.S. Cl.
CPC ............ *H02J 50/20* (2016.02); *A61N 1/3787* (2013.01); *H02J 50/001* (2020.01); *H02J 50/27* (2016.02);
(Continued)

(58) Field of Classification Search
CPC .......... H02J 50/20; H02J 50/27; H02J 50/001; A61N 1/3787
See application file for complete search history.

(56) References Cited

U.S. PATENT DOCUMENTS 6,289,237 B1    9/2001    Mickle et al.
6,615,074 B2    9/2003    Mickle et al.
(Continued)

OTHER PUBLICATIONS

Nimo et al, "Ambient Electromagnetic Wireless Energy Harvesting using Multiband Planar Antenna", 2012, IEEE, International Multi-Conference on Systems, Signals & Devices. Availabe at https://ieeexplore.ieee.org/document/6198036/similar#similar (Year: 2012).*

(Continued)

*Primary Examiner* — Adi Amrany
(74) *Attorney, Agent, or Firm* — Shumaker & Sieffert, P.A.

(57) ABSTRACT

The disclosure describes techniques to provide antennae configured to harvest radio-frequency (RF) energy from the nearby environment to provide electrical energy to an electrically powered device. Antennae may be configured in different shapes, lengths, locations, and materials to efficiently collect RF energy to be converted to electrical power. In some examples, RF energy may be harvested from existing sources, such as FM radio transmissions, communication transmissions such as Wi-Fi and BLUETOOTH, and similar existing sources. In other examples, antennae may be configured to collect energy from a source specifically designated to recharge the device. In some examples, the harvested RF energy may be sufficient to power the device. In other examples, the harvested RF energy may provide enough power to reduce the amount of recharging required by other means, such as by inductive recharging.

20 Claims, 8 Drawing Sheets

(51) Int. Cl.
  *H02J 50/00* (2016.01)
  *A61N 1/378* (2006.01)
  *H04B 5/00* (2006.01)

(52) U.S. Cl.
  CPC ......... *H04B 5/0037* (2013.01); *H04B 5/0081* (2013.01)

(56) References Cited

U.S. PATENT DOCUMENTS

| | | | |
|---|---|---|---|
| 6,856,291 | B2 | 2/2005 | Mickle et al. |
| 7,027,311 | B2 | 4/2006 | Vanderelli et al. |
| 7,057,514 | B2 | 6/2006 | Mickle et al. |
| 7,639,994 | B2 | 12/2009 | Greene et al. |
| 7,643,312 | B2 | 1/2010 | Vanderelli et al. |
| 7,812,771 | B2 | 10/2010 | Greene et al. |
| 7,844,306 | B2 | 11/2010 | Shearer et al. |
| 7,868,482 | B2 | 1/2011 | Greene et al. |
| 7,898,105 | B2 | 3/2011 | Greene et al. |
| 7,925,308 | B2 | 4/2011 | Greene et al. |
| 8,159,090 | B2 | 4/2012 | Greene et al. |
| 8,380,255 | B2 | 2/2013 | Shearer et al. |
| 8,432,062 | B2 | 4/2013 | Greene et al. |
| 8,461,817 | B2 | 6/2013 | Martin et al. |
| 8,621,245 | B2 | 12/2013 | Shearer et al. |
| 9,000,616 | B2 | 4/2015 | Greene et al. |
| 9,021,277 | B2 | 4/2015 | Shearer et al. |
| 10,946,206 | B2 | 3/2021 | Gaddam et al. |
| 11,038,262 | B2* | 6/2021 | Yehezkely ............... H02J 7/02 |
| 2007/0100385 | A1 | 5/2007 | Rawat et al. |
| 2008/0300658 | A1* | 12/2008 | Meskens ............ A61N 1/36036 607/60 |
| 2009/0228074 | A1 | 9/2009 | Edgell et al. |
| 2011/0309686 | A1* | 12/2011 | Scherbenski ........... H02J 50/20 307/104 |
| 2012/0245649 | A1 | 9/2012 | Bohori et al. |
| 2013/0207744 | A1 | 8/2013 | Singh et al. |
| 2013/0261703 | A1 | 10/2013 | Chow et al. |
| 2014/0358195 | A1 | 12/2014 | Sauer |
| 2015/0372541 | A1* | 12/2015 | Guo ....................... H02M 1/32 307/104 |
| 2017/0259072 | A1* | 9/2017 | Newham ........... H04W 12/0431 |
| 2018/0254714 | A1* | 9/2018 | Rangel ...................... H01P 1/20 |
| 2018/0296849 | A1 | 10/2018 | Poon et al. |
| 2019/0009097 | A1* | 1/2019 | Hartley .............. A61N 1/37229 |
| 2019/0074585 | A1* | 3/2019 | Vavelin .................... H01Q 1/52 |
| 2019/0148985 | A1* | 5/2019 | Barukh .................. H01Q 19/30 307/104 |
| 2019/0181685 | A1* | 6/2019 | Su ........................ H04B 5/0062 |
| 2019/0290911 | A1 | 9/2019 | Whitehead et al. |
| 2020/0001089 | A1* | 1/2020 | Chae ...................... A61B 5/318 |
| 2020/0119437 | A1 | 4/2020 | Singh et al. |
| 2020/0197710 | A1* | 6/2020 | Harding .............. A61N 1/3787 |
| 2020/0405239 | A1* | 12/2020 | Trabish ................... H01Q 5/10 |
| 2021/0196963 | A1 | 7/2021 | Gaddam et al. |

OTHER PUBLICATIONS

International Search Report and Written Opinion of International Application No. PCT/US2021/038066, dated Oct. 36, 2021, 14 pp.
Krzysztofik et al., "Fractals in Antennas and Metamaterials Applications," Chapter 3 of Fractal Analysis—Applications in Physics, Engineering and Technology, retrieved from https://www.intechopen.com/books/fractal-analysis-applications-in-physics-engineering-and-technology/fractals-in-antennas-and-metamaterials-applications on Jun. 11, 2020, 39 pp.
Poprzen et al., "Fractal Antennas: Design, Characteristics and Application," University of Banjaluka, 2002, 5 pp. (Applicant points out, in accordance with MPEP 609.04(a), that the year of publication, 2002 is sufficiently earlier than the effective U.S. filing date, so that the particular month of publication is not in issue.).
Bernardi et al., "Specific Absorption Rate and Temperature Elevation in a Subject Exposed in the Far-Field of Radio-Frequency Sources Operating in the 10-900-MHz Range," IEEE Transactions on Biomedical Engineering, vol. 50, No. 3, Mar. 2003, 11 pp.
"PCC110/PCC210 Powerharvester Chipset" POWERCAST, Apr. 2018, 1 pp.
U.S. Appl. No. 17/350,547, filed Jun. 17, 2021, naming inventors Monson et al.

* cited by examiner

1

ANTENNA FOR USE WITH RF ENERGY HARVESTING

This application claims the benefit of U.S. Provisional Patent Application No. 63/041,665 filed on Jun. 19, 2020 and entitled "ANTENNA FOR USE WITH RF ENERGY HARVESTING" the entire contents of each are incorporated herein.

TECHNICAL FIELD

The disclosure relates harvesting radio-frequency energy to power battery operated devices.

BACKGROUND

Rechargeable devices have a benefit that the lifetime power utility is high when compared to devices that use non-rechargeable primary batteries. However, with this benefit may include an inherent burden of the need to spend time to charge the rechargeable power source in the device. In the example of an implanted medical device, the patient may need to remain mostly stationary with a recharging wand, e.g., including an inductive charging coil, held in place near the implanted medical device.

SUMMARY

In general, the disclosure describes techniques to provide an antenna configured system to harvest radio-frequency (RF) energy in the nearby environment to provide electrical energy to a device. Antennae may be configured in different shapes, lengths, locations, and materials to efficiently collect RF energy to be converted to electrical power. In some examples, RF energy may be harvested from existing sources, such as FM radio transmissions, communication transmissions such as Wi-Fi and BLUETOOTH, and similar existing sources. In other examples, antennae may be configured to collect energy from a source specifically designated to recharge the device. In some examples, the harvested RF energy may be sufficient to power the device. In other examples, the harvested RF energy may provide enough power to reduce the amount of recharging required by other means, such as by inductive recharging.

In one example, the disclosure describes to a wireless-power receiving antenna, the antenna comprising: a first portion configured to wirelessly receive RF energy having frequencies in two or more frequency bands; and a second portion configured to operatively couple the first portion to electrically powered circuitry and provide the received RF energy to operate the electrically powered circuitry. The antenna is configured to be mounted on a case containing the electrically powered device. The case defines a first area, and the antenna defines a second area smaller than the first area.

In another example, the disclosure describes wireless power receiving antenna, the antenna comprising: a first portion configured to wirelessly receive radio frequency (RF) energy having frequencies in two or more frequency bands. The two or more frequency bands comprise: a first frequency band of 10 MHz-20 MHz, and a second frequency band of 100 MHz-700 MHz. The antenna further includes a second portion configured to operatively couple the first portion to an electrically powered device and provide the received RF energy to operate the electrically powered device.

In another example, the disclosure describes method for receiving RF energy, the method comprising: receiving, by a first portion of an antenna, radio frequency (RF) energy having frequencies in two or more frequency bands, coupling, by a second portion of the antenna, the RF energy to electrically powered circuitry, converting the received RF energy to electrical energy, operating the electrically powered circuitry using the electrical energy, and charging a rechargeable power source using the electrical energy, wherein the antenna is configured to be mounted on a case containing the electrically powered device. The case defines a first area, and the antenna defines a second area smaller than the first area.

In another example, the disclosure describes method for receiving RF energy, the method comprising: receiving, by a first portion of an antenna, radio frequency (RF) energy having frequencies in two or more frequency bands. The two or more frequency bands comprise: a first frequency band of 10 MHz-20 MHz, and a second frequency band of 100 MHz-700 MHz. The method further includes coupling, by a second portion of the antenna, the RF energy to electrically powered circuitry, converting the received RF energy to electrical energy, operating the electrically powered circuitry using the electrical energy, and charging a rechargeable power source using the electrical energy.

In another example, the disclosure describes system comprising: an implantable medical device; and wireless power receiving antenna, the antenna comprising: a first portion configured to wirelessly receive radio frequency (RF) energy having frequencies in two or more frequency bands. The two or more frequency bands comprise: a first frequency band of 10 MHz-20 MHz, and a second frequency band of 100 MHz-700 MHz. The system also includes a second portion configured to operatively couple the first portion to an electrically powered device and provide the received RF energy to operate the electrically powered device.

The details of one or more examples of the disclosure are set forth in the accompanying drawings and the description below. Other features, objects, and advantages of the disclosure will be apparent from the description and drawings, and from the claims.

DETAILED DESCRIPTION

The disclosure describes techniques to provide antennae configured to harvest radio-frequency (RF) energy in the nearby environment to provide electrical energy to a device. In some examples, RF energy may be harvested from existing sources, while in other examples, antennae may be configured to collect energy from a RF source specifically designated to recharge the device.

In contrast to the techniques of this disclosure, for inductive recharging and similar recharging techniques, in some examples the device may be placed on or near a charging pad. In some examples, such as an implantable medical device, a recharging wand, e.g., including an inductive charging coil, may be held in place near the implanted medical device. Therefore, though rechargeable devices may have an advantage in avoiding the need to change depleted batteries, a rechargeable device, and the recharging coil, either in a wand or on a pad, may need to remain mostly stationary with respect to each other during the charging process because proximity and aspect of the two devices may impact charging efficiency.

However, the techniques of this disclosure may provide advantages which may reduce, or in some examples, eliminate the how often a device may need to be recharged and the length of time needed to recharge a device. Harvesting RF energy may provide a system with a rechargeable power source to recharge without the need to remain stationary in one location during charging. In some examples, a device that includes a RF harvesting antenna of this disclosure may be recharged while still in use and moving with respect to the source of RF energy. In the example of an implantable medical device, the techniques of this disclosure may reduce the burden on the patient to remain stationary during charging and improve quality of life. In other words, the use of radio frequency waves may have advantages because RF energy may travel through human tissue. Because inductive charging is inducing a current in the receiver, the two devices need to be in the proper direction to cause the induced energy, which may benefit from close proximity of the IMD and charging device. In contrast, the techniques of this disclosure may reduce the burden to place an external charging device directly over the IMD. These techniques could for example charge the IMD while the patient sleeps without regard for patient movement during sleep.

Figure 1:
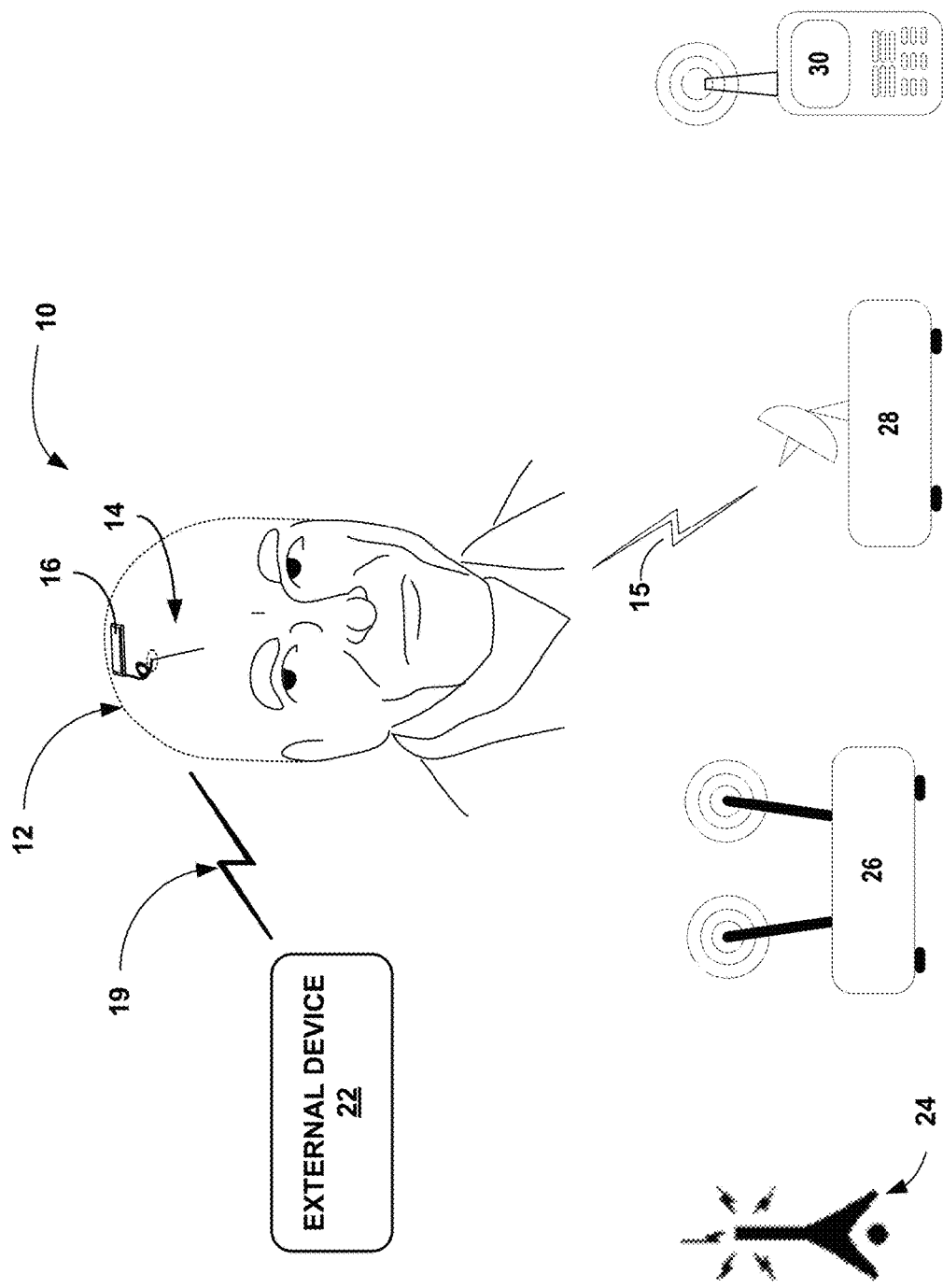
FIG. 1 is a conceptual diagram illustrating an example system that includes an implantable medical device with a rechargeable power source and at least one antenna configured to harvest RF energy to charge the rechargeable power source.

FIG. 1 is a conceptual diagram illustrating an example system 10 that includes an implantable medical device (IMD) 16 with a rechargeable power source and at least one antenna configured to harvest RF energy to charge the rechargeable power source. Although FIG. 1 uses an example of an implantable medical device, the techniques described in this disclosure are generally applicable to a variety of devices powered by a rechargeable power source. Some examples may include other medical devices such as patient monitors, electrical stimulators, or drug delivery devices, as well as non-medical devices such as electronic door locks, smoke and CO2 alarm devices, personal computing device, wearable devices, and so on.

As shown in the example of FIG. 1, system 10 includes an IMD 16 in conjunction with a patient 12, who is ordinarily a human patient. IMD 16 and external device 22 may be communicatively linked via communication/power link 19. Examples of system 10 may also include one or more leads 14, which may be implanted in patient 12 and configured to sense electrical signals within patient 12 as well as carry stimulation pulses from IMD 16. In some examples, leads 14 may also act as an antenna to harvest RF energy. In some examples, system 10 may include other antennae (not shown in FIG. 1) configured to harvest RF energy and add the harvested energy to the rechargeable power source of IMD 16. Other antenna may include an antenna mounted to the housing of IMD 16 and coupled to the rechargeable power source. In some examples, an RF harvesting antenna may be placed on the skin, implanted directly under the skin to reduce attenuation through fatty tissue or implanted in some location on patient 12 external to IMD 16. Also, an external antenna may allow for a larger antenna which may collect more RF energy than a smaller antenna. In other words, an external antenna may allow the antenna to define an area larger than the area defined by the housing of the device.

In some examples, the RF harvesting antenna is a multi-frequency antenna configured to efficiently couple RF energy at multiple frequencies. In some examples, the RF harvesting antenna is a fractal antenna. In other words, a geometry of the RF harvesting antenna comprises a fractal geometry.

Sources of RF energy may be already present in the environment of system 10 and directed to uses other than to recharge a power source. For example, broadcast stations 24 such as FM radio and television may be present in the environment and may be harvested by the RF harvesting antenna of system 10. In other examples, wireless communication such as Wi-Fi broadcast devices 26, mobile phone 30, BLUETOOTH, ZigBee, wireless telephones, and other wireless communication devices may insert RF energy into the environment near system 10. Antennae of system 10 may be configured to harvest RF energy from one or more of these sources at one or more frequencies, as described herein. In some examples, antenna design may be defined by the proximity of certain RF sources. For example, with the prevalence of FM and TV signals in the continental North America, an antenna may be configured to target those frequencies. In other locations, e.g., the Marshall Islands, Europe, and so on, a different set of frequencies may be prevalent. The RF harvesting antenna may be configured to target signals in a specific region.

In other examples, an RF source 28 may be configured to transmit RF energy 15 to the RF harvesting antennae coupled to IMD 16. In some examples, RF source 28 may include an omni-directional antenna used to transmit RF energy 15. In other examples, RF source 28 may include a directional antenna configured to focus RF energy 15 toward the RF harvesting antennae of system 10. In some examples, RF source 28 may include a closed-loop control system to maintain optimal energy transfer between the two devices by orienting the RF energy. In some examples, a directional antenna may be implemented as a phased array antenna. A phased array antenna may be described as a single antenna with multiple antenna elements. In some examples, IMD 16 may provide feedback regarding the effectiveness of the recharging process, which may allow RF source 28 to adjust the transmitted frequency to optimize the recharging process.

A directional antenna for RF source 28 may provide advantages over an omni-directional antenna in that RF source 28 may focus power in a desired direction and thereby reduce the amount energy consumed and transmitted. Other advantages may include reduced interference with other electronic devices near RF source 28. RF source 28 may provide advantages over charging systems that may require a wand, paddle, or similar transmitting device to be held in place over the device to be charged. Instead, the device to be charged need only be within range of the RF energy transmitted by RF source 28.

In some examples, system 10 may also include an external device 22, located externally to patient 12, which may be communicatively coupled via communication link 19 to one or more implanted and/or worn devices of system 10. External device 22 may also be communicatively coupled to external device 22 via communication link 29. As described herein, information may be transmitted between IMD 16 and external device 22 using one or more wireless communication techniques. Examples of communication techniques may include, for example, low frequency or RF telemetry. In some examples, external device 22 may be referred to as a clinician programmer or patient programmer because it is configured to program one or more operations of IMD 16.

In the example illustrated in FIG. 1, IMD 16 is an implantable electrical stimulator that delivers neurostimulation therapy to patient 12, e.g., for relief of chronic pain or other symptoms. Generally, IMD 16 may be a chronic electrical stimulator that remains implanted within patient 12 for weeks, months, or even years. In other examples, IMD 16 may be a temporary, or trial, stimulator used to screen or evaluate the efficacy of electrical stimulation for chronic therapy. IMD 16 is shown in the example of FIG. 1 as implanted on top the cranium of patient 12 coupled to a lead 14 that may provide sensing and therapy for patient 12. In other examples, IMD 16 may be implanted in a subcutaneous tissue pocket, within one or more layers of muscle, or other internal location, with lead 14 tunneled between the brain and IMD 16. IMD 16 may include a rechargeable power source (not shown in FIG. 1).

In some examples external device 22 may include a charging device configured to recharge the power source of IMD 16. In some examples external device 22 may couple to a wand, headset, or similar device (not shown in FIG. 1) that may include one or more antennae and is placed closed to IMD 16 during the charging process. In various examples, transmission of data from the sensors and/or IMD 16 is triggered by a polling by the external device(s) for the sensor signals and/or data, which may occur at some predefined time interval, such as once every minute, or may occur based on other factors determined by external device 22, such as power level, recharging state, and/or temperatures detected by the external device(s) related to the recharging process. Polling as used herein refers to examples where the device performing the polling transmits a request for information to one or more other devices, requesting the one or more other devices respond to the polling request by sending at least a response and/or information back to the device transmitting the request. In non-polling examples, a device may simply transmit data to another device, for example at some predefined time interval, or for example based on some triggering event such as a change in the patient status, without the device that is to receive that transmitted data making a request to have the data transmitted.

In the example of FIG. 1, lead 14 is disposed within patient 12, e.g., implanted within patient 12. In some examples, lead 14 may tunnel through tissue of patient 12 from along spinal cord to a subcutaneous tissue pocket or other internal location where IMD 16 is disposed. Although lead 14 may be a single lead, lead 14 may include a lead extension or other segments that may aid in implantation or positioning of lead 14. In addition, a proximal end of lead 14 may include a connector (not shown) that electrically couples to a header of IMD 16. Although only one lead 14 is shown in FIG. 1, system 10 may include two or more leads, each coupled to IMD 16 and directed to similar or different target tissue sites. For example, multiple leads may be disposed along spinal cord or leads may be directed to spinal cord and/or other locations within patient 12. In some examples one or more lead extensions may also act as an antenna to harvest RF energy.

In alternative examples, IMD 16 and lead 14 may be configured to deliver stimulation energy generated by IMD 16 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 14 and IMD 16 may also be configured to provide other types of electrical stimulation or drug therapy (e.g., with lead 14 configured as a catheter). For example, lead 14 may be configured to provide deep brain stimulation (DBS), peripheral nerve stimulation (PNS), or other deep tissue or superficial types of electrical stimulation. In other examples, lead 14 may provide one or more sensors configured to allow IMD 16 to monitor one or more parameters of patient 12. The one or more sensors may be provided in addition to, or in place of, therapy delivery by lead 14.

Although lead 14 is described as generally delivering or transmitting electrical stimulation signals, lead 14 may additionally or alternatively transmit electrical signals from patient 12 to IMD 16 for monitoring. For example, IMD 16 may utilize detected nerve impulses to diagnose the condition of patient 12 or adjust the delivered stimulation therapy. Sensed signal provided through lead 14 to IMD 16 may also be processed and used to monitor and control a recharging process being used to recharge the rechargeable power source of IMD 16, as further described in this disclosure. As such, lead 14 may thus be used to transmit electrical signals to and from patient 12.

External device 22 may allow a user, such as a clinician or patient 12, to interact with a user interface of an external device 22 to program IMD 16, and/or to otherwise interface with system 10. In some examples, a user interface may include a display screen configured to display information, such as text and/or graphical information, to the user. In some examples, user interface includes an input device, such as a touch screen, that allows a user to provide inputs to the external device 22 and thus to system 10.

IMD 16 include a housing constructed of any polymer, metal, or composite material sufficient to house the components of IMD 16 (e.g., components illustrated in FIG. 2) within patient 12. IMD 16 may be constructed with a biocompatible housing, such as ceramic, titanium or stainless steel, or a polymeric material such as silicone, parylene, or polyurethane, and surgically implanted at a site in patient 12 near the pelvis, abdomen, or buttocks. The housing of IMD 16 may be configured to provide a hermetic seal for components, such as rechargeable power source. In addition, the housing of IMD 16 may be selected of a material that facilitates receiving energy to charge a rechargeable power source. In some examples the housing of IMD 16 may be configured to mount and support an RF harvesting antenna.

In some examples, some RF frequencies may be better suited to pass through human tissue than other frequencies. Some RF frequency bands may be blocked or absorbed by some types of tissue. In other examples, some RF frequencies may cause unwanted heating of human tissue or other unwanted effects. The RF frequencies that pass efficiently through muscle tissue may be different than RF frequencies that pass efficiently through adipose or fatty tissue. In some examples, RF frequencies may be attenuated, refracted, e.g., change direction, frequency shifted or otherwise changed by passing through tissue.

Frequencies may be characterized by a specific absorption rate (SAR), which is a measure of the rate at which energy is absorbed by human tissue when exposed to RF energy. In the example of IMD 16 implanted in muscle tissue, e.g., the buttocks or at the fat-muscle interface, the RF harvesting antenna may be configured to receive a first predetermined frequency band, which may be different than the RF harvesting antenna for a medical device implanted in other locations. In other examples, the RF harvesting antenna may be configured to efficiently receive one or more predetermined frequency bands. In some examples the RF harvesting antenna may be configured to receive frequencies in a first frequency band of 10 to 20 MHz, in a second frequency band of 100 to 700 MHz, as well as other frequency bands, such as frequencies near 2.4 GHz and that includes 2.4 GHz. These frequency bands may have a lower SAR than other frequencies and thus be more appropriate for receiving RF energy within tissue. These frequencies may be lower than 10 MHz, between 20 MHz and 100 MHz, or greater than 700 MHz in other examples, even if the SAR is higher. In some examples, RF harvesting antenna coupled to IMD 16 may be configured to receive one or more sub-bands within the first or second frequency bands and may depend on the implant location.

In other examples, the antenna of IMD 16 may be configured to receive RF energy with frequency in a range of 1 MHz to 1,000 MHz, or even outside of that range. Although SAR values may be higher for some frequencies in this range, the ability to harvest RF energy at these frequencies may contribute to recharge. In one example, the antenna of IMD 16 may be configured to receive RF energy having one or more frequencies within a range from 12 Hz to 16 Hz. In other examples, the antenna of IMD 16 may be configured to receive RF energy having one or more frequencies within a range from 10 Hz to 15 Hz or 1 Hz to 20 Hz. One example frequency for the RF energy may be 13.56 MHz. In some examples, the antenna of IMD 16 is configured to receive RF energy having one or more frequencies within a range from 200 Hz to 500 Hz. In some examples, the antenna of IMD 16 is configured to receive RF energy having one or more frequencies within a range from 250 Hz to 400 Hz. These smaller ranges of frequencies may include frequencies that have lower SAR values than other frequencies outside of the smaller ranges. In one example, the antenna may be configured to receive RF energy having a frequency of approximately 403 MHz. Although an RF signal may include many frequency components, the RF frequencies described herein may be a main frequency at which the RF signals are driven. On a spectral basis, the frequencies of greater power may be those frequencies that fall within the ranges described herein.

In some examples, RF energy passing through human tissue may distort characteristics of the RF energy, similar to how a prism may refract or distort characteristics of light energy passing through the prism. The RF harvesting antennae of this disclosure may be configured to account for any distortion caused by RF energy passing through human tissue. For example, one characteristic of RF energy that may change through human tissue may include a frequency of the RF energy signal. The RF harvesting antenna may be configured to efficiently harvest RF energy that may have a changed frequency after passing through human tissue, such as a change caused by refraction. In this manner, the antenna may be configured to resonate at a frequency that is different than the frequency radiated by an external charging device.

In other examples, the RF harvesting antenna may be configured to harvest energy in the MICS frequency band, which includes frequencies in the range of 402-405 MHz. The Medical Implant Communication Service (MICS) frequency band is reserved for wireless data communications between implanted medical devices and external equipment. However, because MICS band frequencies may already be present near IMD 16, an RF harvesting antenna coupled to IMD 16 may be configured to harvest RF frequencies in the MICS band.

The rechargeable power source may be included within the housing of IMD 16. However, in other examples, the rechargeable power source may be located external to the housing of IMD 16, separately protected from fluids of patient 12, and electrically coupled to electrical components of IMD 16. This type of configuration of IMD 16 and the rechargeable power source may provide implant location flexibility when anatomical space for implantable devices is minimal. In the example of other medical or non-medical devices, the rechargeable power source may be included in the device housing or external to the device. In any case, the rechargeable power source may provide operational electrical power to one or more components of IMD 16, or other devices. Rechargeable power source may include one or more capacitors, batteries, or components (e.g., chemical, or electrical energy storage devices). Example batteries may include lithium-based batteries, nickel metal-hydride batteries, or other materials.

Rechargeable power source may be replenished, refilled, or otherwise capable of increasing the amount of energy stored after energy has been depleted. Rechargeable power source may be subjected to numerous discharge and recharge cycles (e.g., hundreds or even thousands of cycles) over the life of rechargeable power source in IMD 16. Rechargeable power source may be recharged when fully depleted or partially depleted.

External charging circuitry of external device 22 may recharge the rechargeable power source of IMD 16. External device 22 may be a hand-held device, a portable device, or a stationary charging system. In any case, external device 22 may include components necessary to charge the rechargeable power source through tissue of patient 12. For example, when embodied as an external programmer, external device 22 may transmit programming commands to IMD 16 in addition to being configured to recharge the rechargeable power source.

External device 22 may contain processing circuitry, such as a controller (not shown in FIG. 1) that controls delivery of recharge energy through an energy transfer device, such as a wand, headset, or similar device. In other examples, the energy transfer device may be located within the housing of external device 22.

In some examples, external device 22 may include a user interface (not shown in FIG. 1). The user interface may include a display and/or be configured to allow inputs by a user and may provide any of the features and functions described above. External device 22 may be configured to generate electrical power based one or more predefined recharging parameters, wherein the generated electrical power is delivered through a cable the energy transfer device. In various examples, the energy transfer device may include a coil or other winding of an electrically conductive material that acts as the primary coil configured to provide the electrical energy that may be induced into a secondary coil (not shown in FIG. 1) of IMD 16 for the purpose of recharging the power source of IMD 16.

Although RF energy is generally described herein, external device 22 and IMD 16 may use any wireless power transfer techniques or combination of power transfer techniques that are capable of recharging the rechargeable power source of IMD 16 when IMD 16 is implanted within patient 12. In one example, system 10 may utilize inductive coupling between a primary coil (not shown in FIG. 1) of external device 22 and a secondary coil (not shown in FIG. 1) of IMD 16 coupled to the rechargeable power source. In inductive coupling, external device 22, or an energy transfer device connected to external device 22 may be placed near implanted IMD 16 such that a primary coil of external device 22 is aligned with, e.g., placed over, the secondary coil of IMD 16. External device 22 may then generate an electrical current in the primary coil based on a selected power level for recharging the rechargeable power source. In some examples, the power level may be regulated, for example reduced, modulated, or completely removed, based on a detected activity status associated with posture and/or activity level of patient 12.

Communications between IMD 16 and external device 22 may be accomplished using a different set of antennas and/or a different communication format with respect to the coils and format(s) used to provide the electrical energy providing the power transfer between the IMD 16 and external device 22 for the recharging process. In other examples, at least some of the communications between IMD 16 and external device 22 may be accomplished using the same primary coil and the same secondary coil as antennas for the communication as are used for transferring the electrical energy between IMD 16 and external device 22 during the recharging process.

Figure 2:
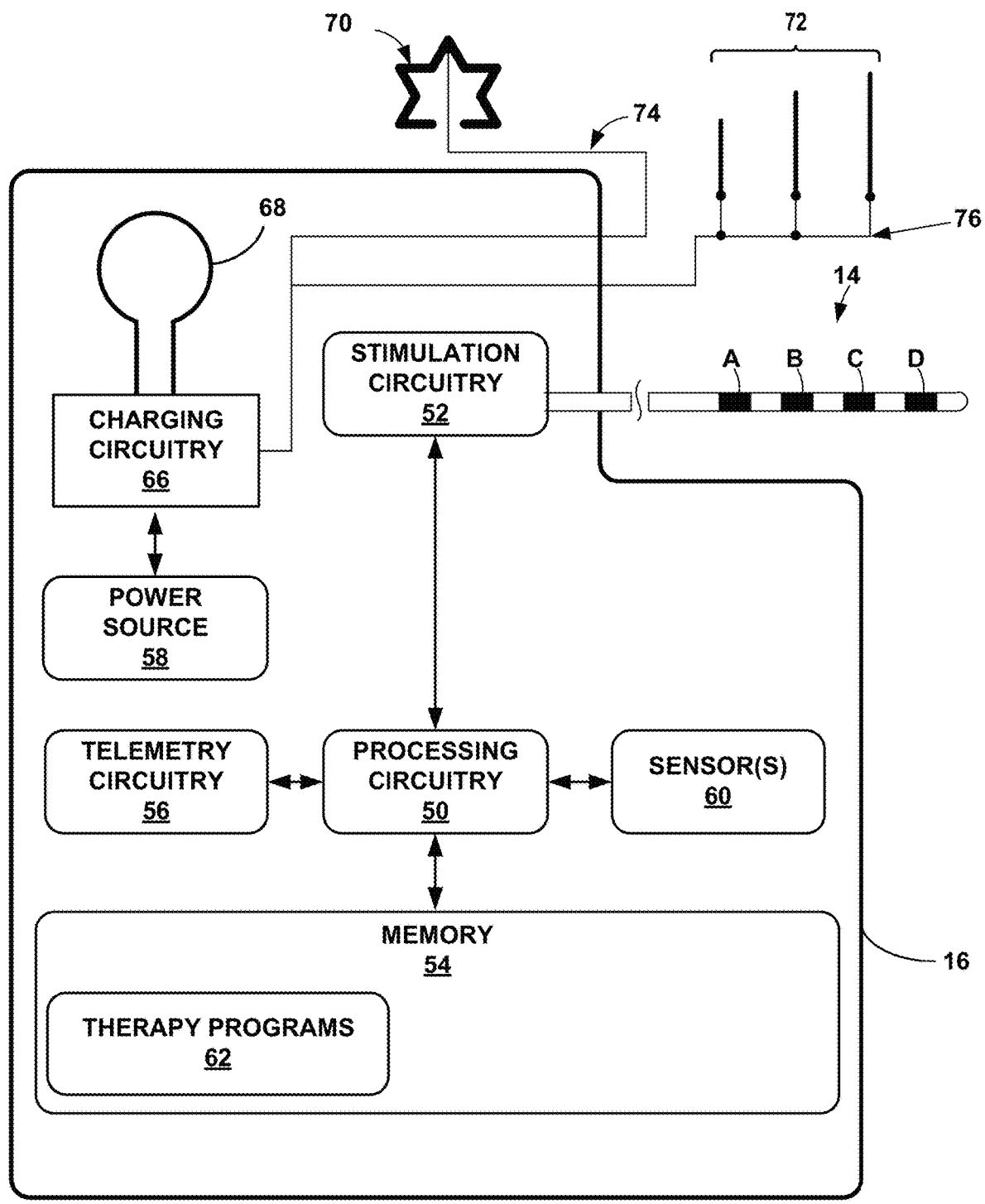
FIG. 2 is a block diagram illustrating example components of a device that includes a rechargeable power source and a RF harvesting antenna, according to one or more techniques of this disclosure.

FIG. 2 is a block diagram illustrating example components of a device that includes a rechargeable power source and at least one RF harvesting antenna, according to one or more techniques of this disclosure. In the example illustrated in FIG. 2, IMD 16 includes processing circuitry 50, memory 54 with therapy programs 62, telemetry circuitry 56, charging circuitry 66, and sensing circuitry 60 (shown as sensor(s) 60 in FIG. 2). IMD 16 also includes the rechargeable power source 58. In other examples, IMD 16 may include a greater or fewer number of components. Also, as described above in relation to FIG. 1, IMD 16 is just one example of a type of rechargeable device that may use the RF harvesting techniques of this disclosure. The techniques described in the example of FIG. 2 may also apply to other medical or non-medical devices.

In other examples, the charging circuitry may be connected to the stimulation circuit directly and the power source may be a primary cell rather than a rechargeable cell. In this manner, the techniques of this disclosure may extend the longevity of a primary cell device. In other examples a device may include be no other power source other than the charging circuitry, e.g., power to an IMD with no power source may be provided via the RF source(s).

In general, IMD 16 may comprise any suitable arrangement of hardware, alone or in combination with software and/or firmware, to perform the various techniques described herein attributed to IMD 16 and processing circuitry 50. In the example of FIG. 2, IMD 16 also includes components to receive power from external sources to recharge the rechargeable power source 58 when rechargeable power source 58 has been at least partially depleted. As shown in FIG. 2, IMD 16 includes secondary coil 68 and charging circuitry 66 coupled to rechargeable power source 58. Charging circuitry 66 may be configured to recharge the rechargeable power source 58 with the selected power level determined by either processing circuitry 50 or external device 20, described above in relation to FIG. 1. Although processing circuitry 50 may provide some commands to charging circuitry 66 in some examples, processing circuitry 50 may not need to control any aspect of recharging. For example, processing circuitry 50 may be configured to provide an output signal, for example sensed values and/or alert signals based on the sensed values, to an external charging device, such as external device 22 shown in FIG. 1, wherein the external charging device is configured to control and modify the recharging process based on the information received from IMD 16.

In other examples, system 10 may include additional modes of sensing the position of the patient and/or device to be charged. Some example techniques may include cameras, microphones, RF triangulation from multiple antennae, and so on. In this manner system 10 may determine the position or approximate position of the device to be charged that would not necessarily involve communication with the device.

Although IMD 16 may use inductive coupling as a one method for recharging rechargeable power source 58, other wireless energy transfer techniques, such as RF energy harvesting described herein, may additionally or alternatively be used. For example, IMD 16 may generally use antenna 70 to harvest RF energy, but IMD 16 may utilize inductive coupling via secondary coil 68 for charging when RF harvesting does not provide sufficient charging. Any recharging techniques may generate heat in IMD 16 such that the charging process may be controlled using a calculated cumulative thermal dose as feedback. In addition, monitored parameters associated with the patient, such as a current posture and/or an activity level associated with the patient while IMD 16 is undergoing a recharging process may also be used to control and/or terminate the recharging process.

In the example of FIG. 2, IMD 16 also includes one or more RF harvesting antennae configured to couple RF energy near IMD 16 to add electrical energy to rechargeable power source 58. In some examples, IMD 16 may connect to one or more dipole antennae 72 of various lengths. Described another way, the one or more dipole antennae 72 may be considered one or more dipole elements of a single antenna or elements of an antenna array.

IMD 16 may alternatively, or in addition, connect to other types of antennae 70. The connected RF antennae may be configured to efficiently harvest the RF energy expected near IMD 16. The antennae of FIG. 2 may include a first portion, e.g., 70 and 72, configured to wirelessly receive RF energy having frequencies in two or more frequency bands. The antennae may also include a second portion, e.g., 74 and 76, configured to operatively couple the first portion to electrically powered circuitry, e.g., charging circuitry 66 and power source 58, and provide the received RF energy to operate the electrically powered circuitry.

The RF harvesting antenna configured to receive RF energy, may be dependent upon the transmitted frequency. For example, FM radio transmission is in Very High Frequency (VHF) band from approximately 47 MHz to 230 MHz as well as the Ultra High Frequency (UHF) frequency band from approximately 470 MHz to 798 MHz. In the example of dipole antennae 72, the length of the antenna is define based on the selected frequency to be harvested, according to the following equation:

$$c = f\lambda$$

where: c=speed of light in air=$2.99705 \times 10^{\wedge}8$ meters/second, f is the frequency in MHz and $\lambda$ is the wavelength in meters. For example, to receive FM radio waves, a whip antenna of 75 cm is equivalent to ¼ wavelength of an FM RF signal. Dipole antennae 72 may include one or more antennae set to various lengths to harvest a desired frequency range. In some examples, dipole antennae 72 may be a conductor included in lead 14. In other examples one or more dipole antennae may be separable from lead 14 to be implanted in nearby tissue. In some examples the dipole antennae may be laid out in various shapes such as a fan, triangle, or other shapes to conform to patient anatomy and to efficiently harvest the RF energy in desired frequency bands. In other examples two or more electrodes (A, B, C or D) of lead 14 may be used as a dipole antenna. In some examples any lead longer than approximately thirty-seven centimeters may be acceptable to harvest RF energy, e.g., from an FM source. In this disclosure, the term "approximately" means within manufacturing or measurement tolerances.

In other examples, other antennae, such as antenna 70 may also be configured to harvest RF energy and couple the RF energy to power source 58, e.g., via charging circuitry 66. In an example in which antenna 70 is a fractal antenna, the size of antenna 70 may be reduced by 50 to 75% of dipole antennae 72, dependent upon the number of fractal iterations. In some examples antenna 70 may be mounted to the inside or the outside of the housing of IMD 16. In some examples, antenna 70 may be mounted on a first side of the housing. In other examples a second antenna, or a second element of antenna 70 may be mounted on a second side of the housing, which may be different from the first side. In other examples, antenna 70 may be mounted such that the antenna wraps around portions of the housing. For example, a housing may have curved portions and the antenna may conform to the curved portions of the housing. In in this disclosure, the housing containing the electrically powered device may also be referred to as a "case" containing the electrically powered device. In the case where antenna 70 is disposed on the outside of the housing, an insulative material may be used to cover antenna 70 so that tissue does not interfere with antenna 70 function. In some examples, the insulative material may keep antenna 70 electrically isolated from the implanted device case. Mounting an antenna, e.g., antenna 70, outside the housing may allow the implanted device to be hermetically sealed in a conductive housing, e.g., extending the antenna outside the faraday cage formed by the conductive housing.

In other examples, antenna 70 may be mounted separately from IMD 16. For example, antenna 70 may be implanted subcutaneously to reduce the amount of human tissue that the RF energy must pass through to reach antenna 70. In this manner, antenna 70 may collect more RF energy when compared to being implanted beneath adipose tissue or some other location.

As described above in relation to FIG. 1, antennae 72 and antenna 70 may be configured to receive a wide bandwidth with multiple frequencies. In some examples, antennae 72 and antenna 70 may be configured to receive specific predetermined frequency bands, such as a first frequency band of 10-20 MHz, and a second frequency band of 100-700 MHz. In other examples, the frequency band may be below, between, or above these example frequency bands. The harvested RF energy may supplement the energy supplied to rechargeable power source 58 via secondary coil 68.

In various examples, processing circuitry 50 of IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components.

IMD 16 also, in various examples, may include a memory 54, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processing circuitry 50, memory 54, therapy programs 62, telemetry circuitry 56, charging circuitry 66, sensor circuitry 60 are described as separate modules or circuits, in some examples, one or more of these modules and/or circuits are functionally integrated.

In some examples, processing circuitry 50, therapy programs 62, telemetry circuitry 56, charging circuitry 66, and sensing circuitry 60 may correspond to individual hardware units, such as ASICs, DSPs, FPGAs, or other hardware units. Each of sensors including in sensing circuitry 60 may generate a signal as a function of one or more physiological parameters of patient 12. Sensing circuitry 60 may include any one or more of activity sensors, such as accelerometers, posture sensors, temperature sensors and other types of sensors. Sensing circuitry 60 may also include analog-to-digital converters (ADC), filters amplifiers and other circuitry configured to receive signals from sensors and convey information to processing circuitry 50. In some examples, IMD 16 may include circuitry (not shown) that conditions the signals generated by sensing circuitry 60 such that they may be analyzed by processing circuitry 50. For example, IMD 16 may include one or more ADCs to convert analog signals generated by these sensors into digital signals usable by processing circuitry 50, as well as suitable filter and amplifier circuitry. IMD may include any number of sensors.

Memory 54 may store therapy programs or other instructions that specify therapy parameter values for the therapy provided by therapy programs 62 and IMD 16. In some examples, memory 54 may also store data such as temperature data, accelerometer data from accelerometer(s) or other sensors and/or data derived from sensing circuitry 60. In some examples, memory 54 stores instructions for recharging rechargeable power source 58, threshold values, and instructions for communication between IMD 16, external device 22, described above in relation to FIG. 1, or any other instructions required to perform tasks attributed to IMD 16.

In this manner, memory 54 may be configured to store information related to determining a status, such as "active" or "inactive" associated with patient 12 during the recharging processes involving IMD 16. Memory 54 may also be configured to store information related to controlling recharging of power source 58 during a recharging process being performed to recharge the rechargeable power source 58. Processing circuitry 50 may be configured to access the information stored in memory 54, and for example in conjunction with sensed values provided by sensing circuitry 60 and/or additional data received through telemetry circuitry 56, to determine a status of a patient during a recharging process involving devices implanted within the patient, and to control the recharging process based at least in part on these status determinations. The additional data received through telemetry circuitry 56 may include signals and/or data generated by sensors outside IMD 16.

In some examples, therapy programs 62 may generate and deliver electrical stimulation under the control of processing circuitry 50. In some examples, processing circuitry 50 controls therapy programs 62 by accessing memory 54 to selectively access and load programs from therapy programs 62. In some examples therapy programs 62 may be configured to deliver drug delivery therapy via a drug reservoir and catheter (not shown). These and other therapies may be provided by IMD 16.

As shown in FIG. 2, secondary coil 68 may include a coil of wire or other device capable of inductive coupling with a primary coil disposed external to patient 12. Although secondary coil 68 is illustrated as a simple loop of in FIG. 2, secondary coil 68 may include multiple turns of wire. In FIG. 2, secondary coil 68 may include a winding of wire configured such that an electrical current can be induced within secondary coil 68 from a magnetic field. The induced electrical current may then be used to recharge rechargeable power source 58. In this manner, the electrical current may be induced in secondary coil 68 associated with rechargeable power source 58. The induction may be caused by electrical current generated in the primary coil of an external device, such as external device 22 as shown in FIG. 1 and based on the selected power level. The coupling between secondary coil 68 and the primary coil of external device 22 may be dependent upon the alignment of the two coils. Generally, the coupling efficiency increases when the two coils share a common axis and are in close proximity to each other. External device 22 and/or IMD 16 may provide one or more audible tones or visual indications of the alignment.

Charging circuitry 66 may include one or more circuits that filter and/or transform the electrical signal induced in secondary coil 68 to an electrical signal capable of recharging the rechargeable power source 58. For example, in alternating current induction, charging circuitry 66 may include a half-wave rectifier circuit and/or a full-wave rectifier circuit configured to convert alternating current from the induction to a direct current for rechargeable power source 58. The full-wave rectifier circuit may be more efficient at converting the induced energy for rechargeable power source 58. However, a half-wave rectifier circuit may be used to store energy in rechargeable power source 58 at a slower rate. In some examples, charging circuitry 66 may include both a full-wave rectifier circuit and a half-wave rectifier circuit such that charging circuitry 66 may switch between each circuit to control the charging rate of rechargeable power source 58 and temperature of IMD 16.

In some examples, charging circuitry 66 may include a measurement circuit configured to measure the current and/or voltage induced during inductive coupling. This measurement may be used to measure or calculate the power transmitted to IMD 16 from external device 22. In some examples, the transmitted power may be used to approximate the temperature of IMD 16 and that of the surrounding tissue. This method may be used to indirectly measure the temperature of tissue in contact with the housing of IMD 16. In other examples, IMD 16 may estimate the transmitted power using the measured voltage or current after charging circuitry 66 or the charging rate of rechargeable power source 58.

Rechargeable power source 58 may include one or more capacitors, batteries, or other energy storage devices. Rechargeable power source 58 may then deliver operating power to the components of IMD 16. In some examples, rechargeable power source 58 may include a power generation circuit to produce the operating power. Rechargeable power source 58 may be configured to operate through hundreds or thousands of discharge and recharge cycles. Rechargeable power source 58 may also be configured to provide operational power to IMD 16 during the recharge process. In some examples, rechargeable power source 58 may be constructed with materials to reduce the amount of heat generated during charging. In other examples, IMD 16 may be constructed of materials that may help dissipate generated heat at rechargeable power source 58, charging circuitry 66, and/or secondary coil 68 over a larger surface area of the housing of IMD 16.

Although rechargeable power source 58, charging circuitry 66, and secondary coil 68 are shown as contained within the housing of IMD 16, at least one of these components may be disposed outside of the housing. For example, secondary coil 68 may be disposed outside of the housing of IMD 16 to facilitate better coupling between secondary coil 68 and the primary coil of external device 22. These different configurations of IMD 16 components may allow IMD 16 to be implanted in different anatomical spaces or facilitate better inductive coupling alignment between the primary and secondary coils. In the example of other medical or non-medical devices, rechargeable power source 58, charging circuitry 66, and secondary coil 68 may either be contained within the housing or be external to the device.

IMD 16 may also include one or more temperature sensors (e.g., thermocouples or thermistors) as part of sensors 60 and be configured to measure the temperature of IMD 16. The temperature sensors may be disposed internal of the housing of IMD 16, contacting the housing, formed as a part of the housing, or disposed external of the housing. The temperature sensors may be used to directly measure the temperature of IMD 16 and/or tissue surrounding and/or contacting the housing of IMD 16. Alternatively, the temperature sensors may be of a type that need not be thermally coupled to housing to sense the housing temperature. Processing circuitry 50, or external device 22, may use this temperature measurement as the tissue temperature feedback to determine the cumulative thermal dose provided to tissue during charging of rechargeable power source 58. Although a single temperature sensor may be adequate, multiple temperature sensors may provide a better temperature gradient or average temperature of IMD 16. The various temperatures of IMD 16 may also be modeled and provided to determine the cumulative thermal dose. Although processing circuitry 50 may continually receive temperature measurements, processing circuitry 50 may conserve energy by only measuring temperature during recharge sessions. Further, temperature may be sampled at a rate necessary to calculate the cumulative thermal dose, but the sampling rate may be reduced to conserve power as appropriate.

Processing circuitry 50 may also control the exchange of information with external device 22 and/or an external programmer using telemetry circuitry 56. Telemetry circuitry 56 may be configured for wireless communication using radio frequency protocols or inductive communication protocols. Telemetry circuitry 56 may include one or more antennas (not shown in FIG. 2) configured to communicate with external device(s), such as external device 22. In some examples, the RF harvesting antennae may be configured to harvest the energy used by telemetry circuitry 56. Communications that are performed by telemetry circuitry 56 may be performed using a separate antenna, using secondary coil 68 as an antenna, or using a combination of the coil and antenna.

Figure 3A:
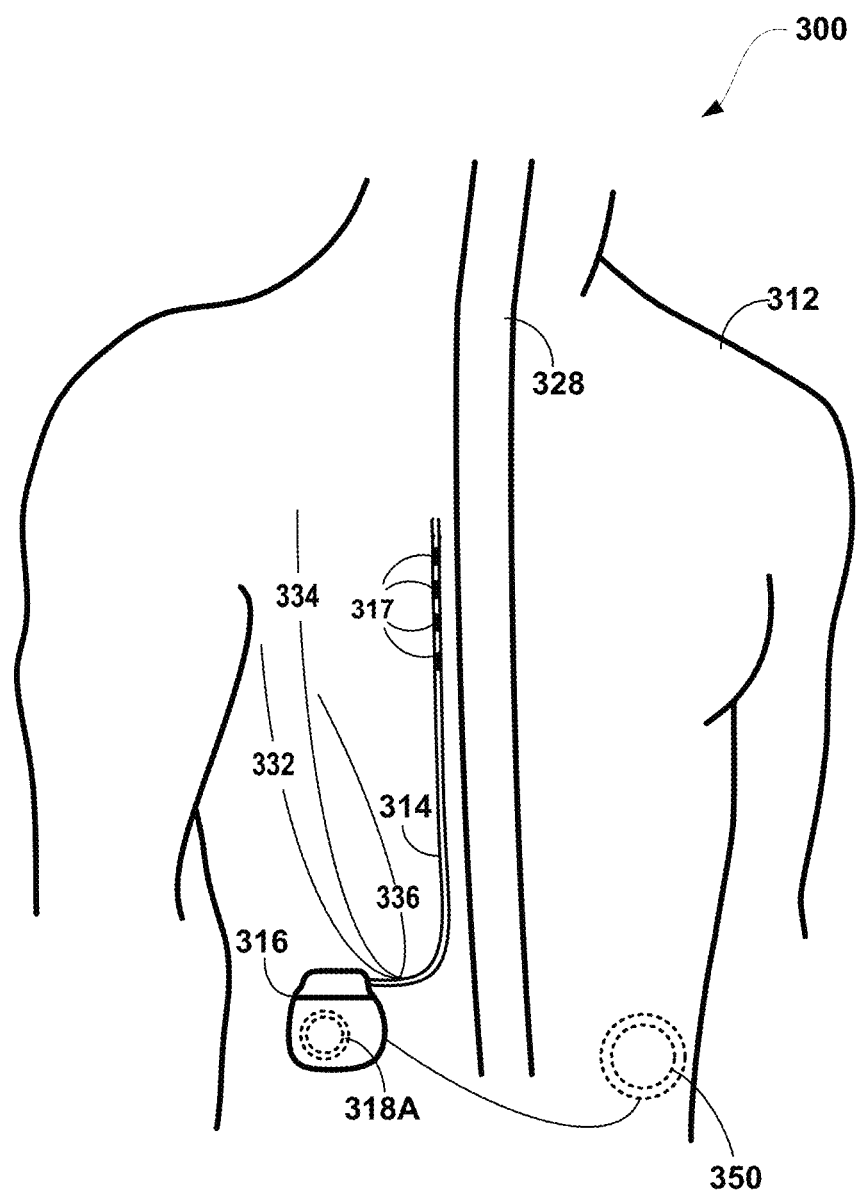
FIG. 3A is a conceptual diagram illustrating an example system that includes an implantable medical device with a rechargeable power source and RF harvesting antennae.

FIG. 3A is a conceptual diagram illustrating an example system 300 that includes an implantable medical device IMD 316 with a rechargeable power source. IMD 316, lead 314 with electrodes 317 are examples of respectively, IMD 16, lead 14 and electrodes A-D described above in relation to FIGS. 1 and 2 and have the same characteristics and functions described above.

In the example of FIG. 3A, lead 314 is disposed within patient 312, e.g., implanted within patient 312. Lead 314 may tunnel through tissue of patient 312 from along spinal cord to a subcutaneous tissue pocket or other internal location where IMD 316 is disposed. Although lead 314 may be a single lead, lead 314 may include a lead extension or other segments that may aid in implantation or positioning of lead 314. In addition, a proximal end of lead 314 may include a connector (not shown) that electrically couples to a header of IMD 316. Although only one lead 314 is shown in FIG. 3A, system 300 may include two or more leads, each coupled to IMD 316 and directed to similar or different target tissue sites. For example, multiple leads may be disposed along spinal cord or leads may be directed to spinal cord and/or other locations within patient 312 when IMD 316 is configured to deliver spinal cord stimulation. However, in cases where IMD 316 is implanted to provide DBS therapy or other therapies to other locations, including one or more nerves of the pelvic floor and the tibial nerve, IMD 316 may use similar antennae as shown in FIG. 3A and/or one or more of leads to harvest RF energy.

In some examples, system 300 may include one or more separated antennae connected to IMD 316. IMD 316 may include one or more ports, e.g., one or more connectors on the header of IMD 316, to connect separated antenna 350 to the circuitry of IMD 316. Separated antenna 350 may allow the antenna to be connected to IMD 316 through a port similar to how leads are connected as shown in FIG. 3A. Separated antenna 350 may be configured for harvesting RF signals for recharging or for receiving or transferring communication data. Separated antenna 350 may be implanted proximal to IMD 316 in some examples. In other examples, separated antenna 350 may be implanted in a different location. In other examples, separated antenna 350 may be located outside of the body of patient 312, such as worn by or attached to the skin of patient 312, and connected to IMD 316 via a percutaneous connector. In some examples, separate antenna 350 may be used to manage the temperature of IMD 316, for example, during recharging.

In some examples, separated antenna 350 may provide advantages compared to other antenna configurations, such as an internal antenna, or an antenna on the separated surface of IMD 316. In some examples, separated antenna may be placed close to the surface of the skin and therefore may be subject to less of an impact from tissue absorption of RF energy, and thus may be more effective than an antenna located within or on the surface of the housing of IMD 316. In addition, when harvesting in different radio environments, different antennae, e.g., different shapes, sizes and so on may provide more options depending on the radio environment. For example, separated antenna 350 may be larger than the housing of IMD 316 and therefore might be more effective in some environments. Separated antenna 350 may be any shape, e.g., a fractal shape, as described above in relation to FIG. 1.

As described above in relation to FIGS. 1 and 2, one or more of leads 314, or lead extensions, may also act as a RF harvesting antenna to couple RF energy to the rechargeable source of IMD 316. In other examples, one or more dipole antennae, 332, 334 and 336 may also harvest RF energy for IMD 316. As shown in the example of FIG. 3A, dipole antennae 332, 334 and 336 may connect to IMD 316 via the same header used by lead 314. In some examples, dipole antennae 332, 334 and 336 may be configured as a lead extension of lead 314. In other examples, lead 314 may include one or more dipole antennae within the body and the conductive sheath of lead 314 (not shown in FIG. 3A). In some examples, lead 314 may include shielding for the electrical conductors connected to leads 314 (not shown in FIG. 3A). In some examples, the shielding for lead 314 may act as an RF harvesting antenna. The one or more dipole antennae 332, 334 and 336 may be arranged in locations on patient 312 to harvest RF energy based on the most likely sources of RF energy expected near system 300. In other examples, an RF harvesting antenna may be placed on, or molded within the header of IMD 316, e.g., stamped, or printed metal within a polysulfone polymeric material.

Lead 314 may carry one or more electrodes, such as electrodes 317, that are placed adjacent to the target tissue, e.g., spinal cord for spinal cord stimulation (SCS) therapy. One or more electrodes may be disposed at a distal tip of lead 314 and/or at other positions at intermediate points along lead 314, for example. Electrodes 317 of lead 314 transfer electrical stimulation generated by an electrical stimulation generator in IMD 316 to tissue of patient 312. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar, or multipolar electrode configurations for therapy. In general, ring electrodes arranged at different axial positions at the distal ends of lead 314 will be described for purposes of illustration.

As described above in relation to FIG. 2, IMD 316 may also include other antennae, such as antenna 318A. In some examples, IMD 316 may include two or more antennae 318A, e.g., mounted on either side of the housing of IMD 316. The geometry of antenna 318A may comprise a fractal geometry and be configured to harvest RF energy in one or more RF frequency bands.

IMD 316 may be constructed of any polymer, metal, ceramic, or composite material sufficient to house the components of IMD 316 (e.g., components illustrated in FIG. 2) within patient 312. IMD 316 may be constructed with a biocompatible housing, such as titanium or stainless steel, ceramic, or a polymeric material such as silicone, polysulfone, or polyurethane, and surgically implanted at a site in patient 312 near the pelvis, abdomen, or buttocks. The housing of IMD 316 may be configured to provide a hermetic seal for components, e.g., components described above in relation to FIG. 2. In addition, the housing of IMD 316 may be selected of a material that facilitates receiving energy to charge the rechargeable power as described above in relation to FIG. 1.

In some examples, antenna 318A may be enclosed, e.g., encased, in a polymer, composite or other non-conductive material that may provide protection for antenna 318A, be RF transparent and provide isolation from the housing of IMD 316. In some examples, antenna 318A may be located at a specified distance from the housing of IMD 316 such that the housing acts as a reflector to enhance the collection of RF energy by antenna 318A. In other examples, antenna 318A may be separate from the housing of IMD 316, as described above in relation to FIG. 2.

Figure 3B:
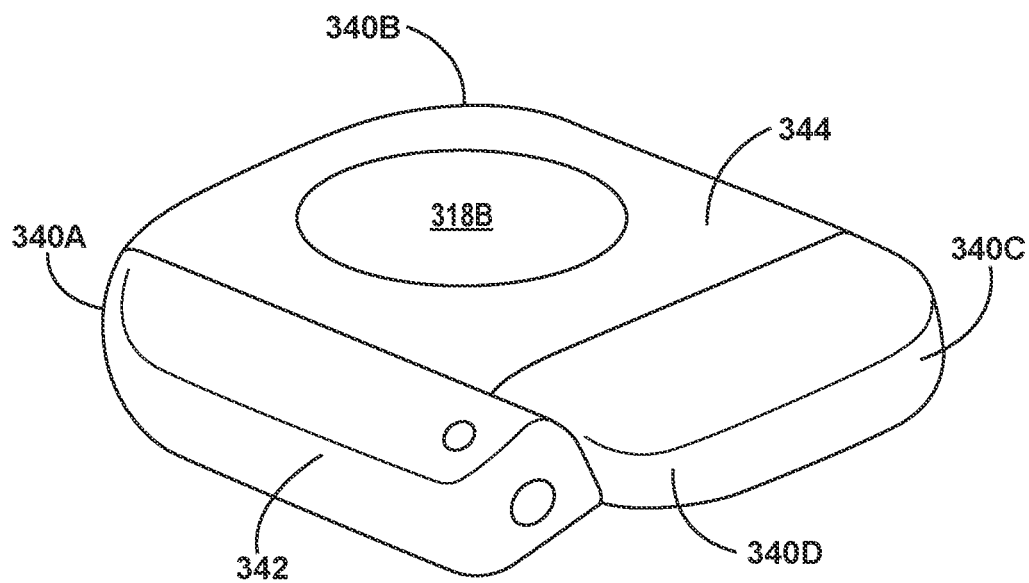
FIG. 3B is a conceptual diagram illustrating an isometric view of an example implantable medical device with a rechargeable power source and RF harvesting antennae.

FIG. 3B is a conceptual diagram illustrating an isometric view of an example implantable medical device with a rechargeable power source and RF harvesting antennae. The example IMD of FIG. 3B includes RF harvesting antenna 318B, which corresponds to antenna 318A described above in relation to FIG. 3A. Antenna 318B may be printed on or otherwise attached to housing 344. The IMD may also include rounded corners 340A, 340B, 340C and 340D (collectively corners 340), and header 342.

Figure 3C:
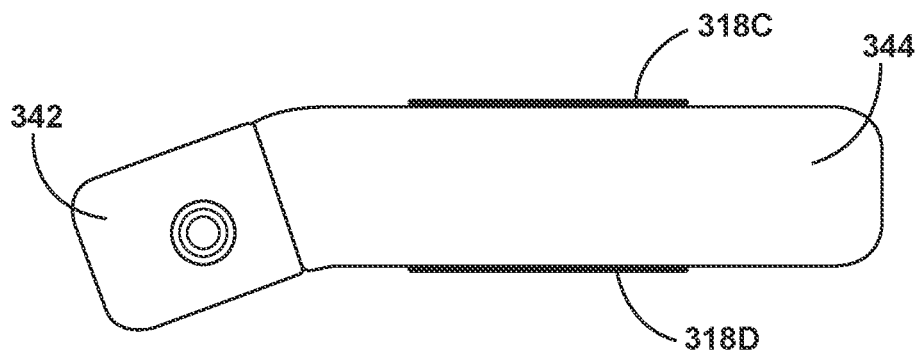
FIG. 3C is a conceptual diagram illustrating an example implantable medical device with a rechargeable power source and RF harvesting antennae on each side of the device.

FIG. 3C is a conceptual diagram illustrating an example implantable medical device with a rechargeable power source and RF harvesting antennae on each side of the device. The IMD of FIG. 3C includes header 342 and antennae 318C and 318D attached to either side of housing 344. Either of antennae 318C and 318D may correspond to antenna 318A or 318B described above in relation to FIGS. 3A and 3B. In other examples, the antennae may be interwoven in the entire enclosure all around the entire surface of the device. In some examples, the antennae may be a printed fractal antenna, or other type of antenna, that is printed on multiple sides, or all sides of housing 344, resulting in a more unidirectional communication and recharging capability. Printed an antenna may refer to a wide range of techniques are used to print electrical devices onto a substrate. In the example of FIG. 3C, a substrate may include any substance that the printing process takes place on such as directly on housing 344, a label to be applied to housing 344, a shrinkable material that may be attached to housing 344, and so on. Some examples techniques may include screen printing, photolithography, inkjet, 3D printing, and other related techniques. Inks used in printing may include conductive material such as metallic or electrically conductive nanoparticles, or similar materials, which can be printed in an arbitrary pattern.

In some examples of electrically conductive nanomaterials, a high percent loading and low porosity may yield a desirable performance. For example, a 3D printed structure with carbon nanotubes (CNT) or silver nanowires (AgNW) may be printed to be tens to hundreds of microns thick and with a density of greater than 90% in the areas where the conductive structures are desired. In other examples, traditional materials like copper, gold, or silver may serve the same intended purpose as nanomaterials for an antenna, in examples in which the desired antenna structure can be realized while still maintaining biocompatibility. In some examples, to maintain biocompatibility, as well as ensure RF performance, the antenna, whether of nanomaterials or traditional materials, may be surrounded by dielectric material, for example polysulfone or parylene.

Similar to the other antennae in FIGS. 3A-3D, in some examples, antennae 318C and 318D, may be electrically connected, either outside housing 344, at the internal circuitry of the IMD, at the connection that passes from outside the housing to inside the housing, e.g., at header 342, or some other location. In other examples, the antennae of FIGS. 3A-3D, when used in combination with each other, may individually connect to charging circuitry of the IMD.

Figure 3D:
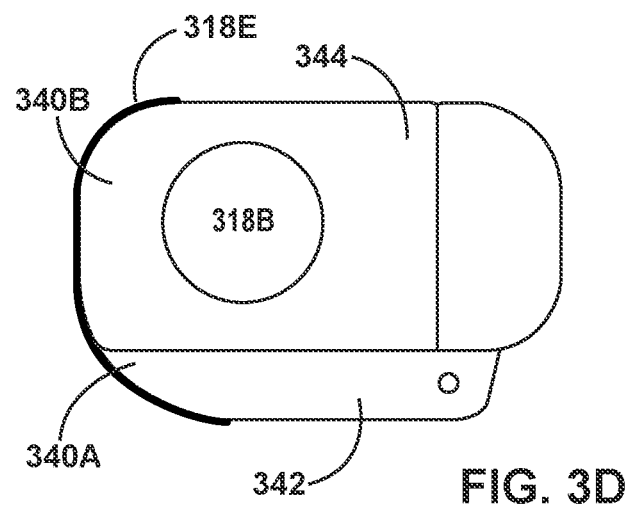
FIG. 3D is a conceptual diagram illustrating an example implantable medical device with a rechargeable power source and an RF harvesting antenna on a curved portion of the device.

FIG. 3D is a conceptual diagram illustrating an example implantable medical device with a rechargeable power source and an RF harvesting antenna on a curved portion of the device. In the example of FIG. 3D, antenna 318E is attached to housing 344 and conforms to rounded corners 340B and 340A of housing 344 as well as part of header 342.

In other examples, not shown in FIGS. 3A-3D, an RF harvesting antenna may be mounted within or attached to header 342 without touching housing 344. In other examples a housing of an IMD may have a cylindrical or similar curved surface with an RF harvesting antenna attached to or printed on the surface of the housing.

Figure 4A:
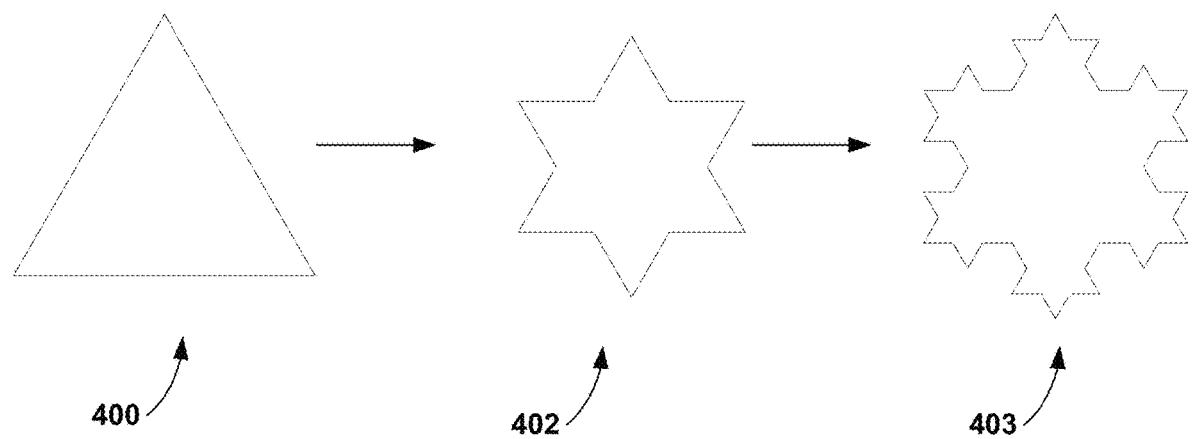
FIG. 4A is a conceptual diagram illustrating example fractal antennae of increasing complexity.

FIG. 4A is a conceptual diagram illustrating example fractal antennae of increasing complexity. Combining multiples of a basic triangle shape 400, may form a star 402 or snowflake 403. Adding additional shapes, may result in a more complex antenna configured to operate at multiple frequencies. The snowflake design of FIG. 4A is only one example arrangement of a fractal antenna. A fractal antenna may be implemented by many other shapes and arrangements. Other types of fractal antennae (not shown in FIGS. 4A and 4B) may include a planar array, a Minkowski island, the Sierpinski triangle, along with a variety of arrangements, e.g., loops, and combinations of similar antennae.

The use of a fractal antenna may allow a smaller antenna profile to be used, when compared to a dipole antenna array. Also, a fractal antenna may increase the bandwidth of the RF signals that can be harvested. In this manner, the increased bandwidth of the single antenna may be able to receive more energy from a multitude of sources for energy harvesting. In some examples, a fractal antenna may be configured to receive portions of the VHF, UHF, and other bands, which may have the advantage of harvesting existing radiation near the antenna. In some examples, a single fractal antenna may be configured to harvest RF energy in one or more specified frequency bands. For example, the fractal antenna may be configured to harvest energy in a first frequency band of 10-20 MHz, and a second frequency band of 100-700 MHz by selecting the fractal shape and arrangement. In other examples, two or more fractal antennae may be configured as an antenna array to collect RF energy in specified frequency bands.

As described above in relation to FIG. 3A, in some examples a fractal antenna may be printed on the outside of the housing for an IMD, such as IMD 316. In some examples the antenna may be conformally coated to accomplish reception. For an antenna printed on or otherwise attached to the housing of a device, such as an IMD, the size of the antenna may fit within the confines of the size of the housing. In other words, for the antenna that is configured to be mounted on a case containing the electrically powered device, the case may define a first area, and the antenna may define a second area smaller than or equal to the first area.

In some examples an antenna may be implemented on multiple planes. In the example of a fractal antenna, some portions or "legs" of the antenna may be printed or placed on a first layer. Other portions, or legs of the antenna, may be printed or placed on a second layer different from the first layer. In some examples, legs of the antenna on different layers may overlap. In other words, some portion of an antenna on a first layer may overlap portions of the antenna on a second layer. In other examples, the legs of the antenna may be separate without overlapping. These different layers of the antenna may then be electrically connected.

In some examples, the antenna of this disclosure may be configured for multiple uses. In other words, a fractal antenna may be configured to send and receive communication frequencies as well as to harvest RF energy in frequencies different from the communication frequencies.

For example, a broad band antenna may be configured to communicate via BLUETOOTH frequencies as well as harvest RF frequencies in other frequency ranges. The antenna may be configured to have a specific size, shape, length of the legs and so on in order for the antenna to communicate using, as well as harvest, specific frequencies, or ranges of frequencies.

In some examples, shape and size attributes, as well as the location of the antenna on housing 344 may be tuned so that the antenna is effective when working with a reflector. In some examples, a patient may wear, or be located near a reflector configured to reflect RF energy toward the antenna of IMD 316, thereby increasing the amount of RF energy that impinges one or more of antennae 318A, 350 or a lead acting as an antenna. For example, a patient may wear a garment in which a portion of the garment that includes a material that reflects RF energy. For example, a sock or legging may include reflective material partway around the circumference of the patient's tibial area to reflect and focus RF energy toward the antenna. In other examples, a patient may wear a reflector that is located around the region that has the implant, such as an article of clothing, in a bedsheet or something similar. I would think of this as a tube of reflector material worn around the torso, ankle, etc., with a hole in it for the recharge energy to enter, and then it could bounce around inside until it escapes or is absorbed.

Figure 4B:
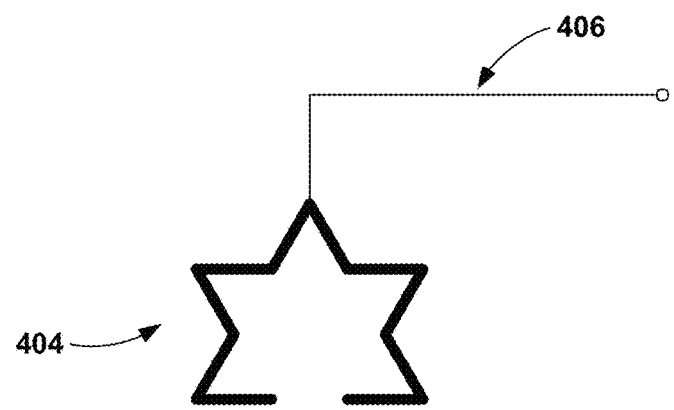
FIG. 4B is a conceptual diagram illustrating an example fractal antenna based on the Koch snowflake fractal antenna.

FIG. 4B is a conceptual diagram illustrating an example fractal antenna based on the Koch snowflake fractal antenna. In some examples the fractal antenna illustrated in FIG. 4B may provide improved bandwidth of received energy when compared to a traditional antenna. The example fractal antenna illustrated by FIG. 4A may increase energy transfer by a factor of three, while the size may be approximately half that of a conventional antenna. Similar to antennae 70 and 72 depicted in FIG. 2, the antenna of FIG. 4A includes a first portion 404 configured to wirelessly receive RF energy having frequencies in two or more frequency bands and a second portion 406 configured to operatively couple the first portion to electrically powered circuitry and provide the received RF energy to operate the electrically powered circuitry.

As described above in relation to FIGS. 1 and 2, selecting the material of the housing, the material of the antenna, the material of any protective covering or coating for the antenna and housing and the arrangement of the antenna in relation to the housing may impact the frequency band and efficiency of the antenna to harvest RF energy. Also, as described above, in the example of an IMD, selection the implant location of the antenna, e.g., in muscle tissue, adipose tissue, subcutaneous, and so on, may impact the frequency band that the antenna may collect, based on tissue penetration and absorption of RF energy.

Figure 4C:
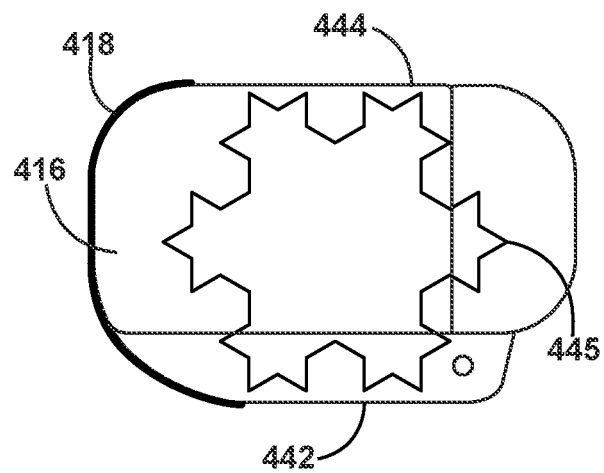
FIG. 4C is a conceptual diagram illustrating an example implantable medical device with heat pipes on the medical device and configured to move heat from one location to another location.

FIG. 4C is a conceptual diagram illustrating an example implantable medical device with heat pipes on the medical device and configured to draw heat from one location to another location. In some examples, the heat pipes 445 may also form the shape of an antenna and perform a dual role as an antenna as well as to transfer heat. The example of FIG. 4C depicts heat pipes 445 on the medical device and located external to housing 444. In other examples, the heat pipes may be internal to IMD 416 or at least connected to the void of space which contains the circuitry of IMD 416 and power source of IMD 416. As described above, for example, in relation to FIG. 1, for an internal antenna, housing 444 may be formed of ceramic or some other non-conductive and biocompatible material.

For an external heat pipe, the antenna/heat pipe 445 may be manufactured external to the body of the device in a polysulfone encasement, but the antenna itself may be hollow so that it can also serve as a heat pipe and the point at which it connects to the internals of the IMD would have an opening that heat pipe 445 would connect to the void of IMD 416. In this manner, when the internals of the IMD heat up the heat pipes would transport thermal energy to the lowest temperature portion of the IMD and distribute the energy around the IMD.

Figure 4D:
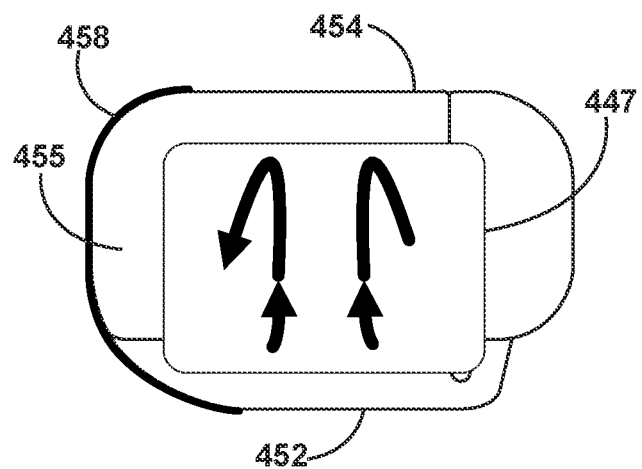
FIG. 4D is a conceptual diagram illustrating an example implantable medical device with one or more vacuum chambers on the medical device and configured to move heat from one location to another location.

The example of FIG. 4C includes IMD 416 with header 442 and antennae 418 and heat pipes 445 attached to housing 444. IMD 416 and IMD 455 in the examples of FIGS. 4C and 4D are similar to the IMDs described above in relation to FIG. 3B-3D. For example, antennae 418, 458 and heat pipes 445 may perform similar to antenna 318A or 318B described above in relation to FIGS. 3A and 3B.

Heat pipes 445 may be a passive heat transfer device that transfers heat by the evaporation and condensation of a two-phase working fluid. In regions of higher temperature, the fluid, in liquid form, may evaporate to a gaseous form absorbing energy from that region, e.g., from header 442, by latent heat of vaporization. The evaporation increases the pressure, forcing the now gaseous fluid to other regions or segments of the heat pipe. At cooler regions of IMD 416, the fluid may condense into liquid and removes heat by dissipation to the colder environment. In some examples, the internal portion of heat pipes 445 may be constructed to include a porous wick structure that is saturated with liquid working fluid. Capillary forces in the wick return the condensate to the evaporator (warmer area), where the cycle repeats. In other examples, heat pipes 445 may include grooves instead of a wick structure. The condensed working fluid may travel back to the evaporator along the grooves by similar capillary forces.

Though shown as a single loop in the example of FIG. 4C, heat pipes 445 may be configured as one or more single lengths of heat pipe. In some examples, heat pipes 445 may include sections of heat pipes that are electrically connected, and the sections may perform as a single antenna, but the fluid is isolated between the sections. In other examples, check valves or similar devices may allow the working fluid to move between individual sections. In other examples, heat pipes 445 may connect to a fluid reservoir, external or internal to housing 444. Though shown as exterior to housing 444, in other examples, heat pipes 445 may be located within housing 444.

The working fluid of heat pipes 445 may be selected to evaporate and condense at specific temperatures, e.g., temperatures that are compatible with the surrounding tissue. Also, adjusting the pressure within heat pipes 445 may adjust the operating temperatures for the working fluid. In this disclosure, the working fluid may also be referred to as a phase change material.

In some examples, various mixtures of working fluid may be combined to set the operating temperatures for evaporation and condensation. In some examples the working fluid may include water, although some materials like alcohol may be used. In other examples, other materials may have specific operating temperatures. For example, a first working fluid may evaporate at 30° C., while a second working fluid may evaporate at 39° C. at the same pressure. Combining the first working fluid and second working fluid in selected proportions may result in a working fluid mixture that evaporates, for example at 35° C. Note that the vacuum in the pipe may be set to establish an equilibrium between the vapor and liquid, such that a mixture of vapor and liquid results in the hot zones being wetted by liquid, and the cold zones condensing the vapor. In some examples approximately 30% liquid, or a range of 25%-40% liquid may provide good results for an implanted medical device in contact with tissue.

In some examples, portions of a heat transfer device may be separate from the medical device, as described above for IMD 316 and separate antenna 350 in relation to FIG. 3A. In some examples, a tube may connect an external condensing portion of a heat transfer device to the IMD. The connecting tube may be plastic, or similar material, with a melting point higher than the vaporization point of the liquid phase change material used. The external condensing portion may be located at a separated thermal discharge area of patient 312, depicted in FIG. 3A, so if IMD 316 increases in temperature, such as during inductive charging, then the heat may be redirected to an area some distance away from IMD 316. In some examples, the separated portion and/or connecting tube may be a conductive material and may act as an antenna independent of the heat transfer, as described above in relation to FIGS. 3A-3D. The condensing portion may be part of a heat pipe matrix and shaped, for examples, as a fractal antenna, and be external to IMD 316 with an electrical connection to the antenna input on IMD 316.

FIG. 4D is a conceptual diagram illustrating an example implantable medical device with one or more vacuum chambers on the medical device and configured to draw heat from one location to another location. Similar to heat pipes 445 described above in relation to FIG. 4C, vacuum chamber 447 may include a working fluid selected to evaporate and condense at specific temperatures. In the example of FIG. 4D, header 452 may be a warmer area compared to other portions of housing 454. The working fluid may evaporate from the warmer area, as shown by the arrows on vacuum chamber 447, and transfer heat to other portions of housing 444 as the working fluid condenses back to a liquid. In some examples, vacuum chamber 447 may include a wicking material, or similar mechanism, to allow the condensed working fluid to return to the warmer region. Similar to heat pipes 445 described above in relation to FIG. 4C, though shown as exterior to housing 444, in other examples, vacuum chamber 447 may be located within housing 444.

Figure 5A:
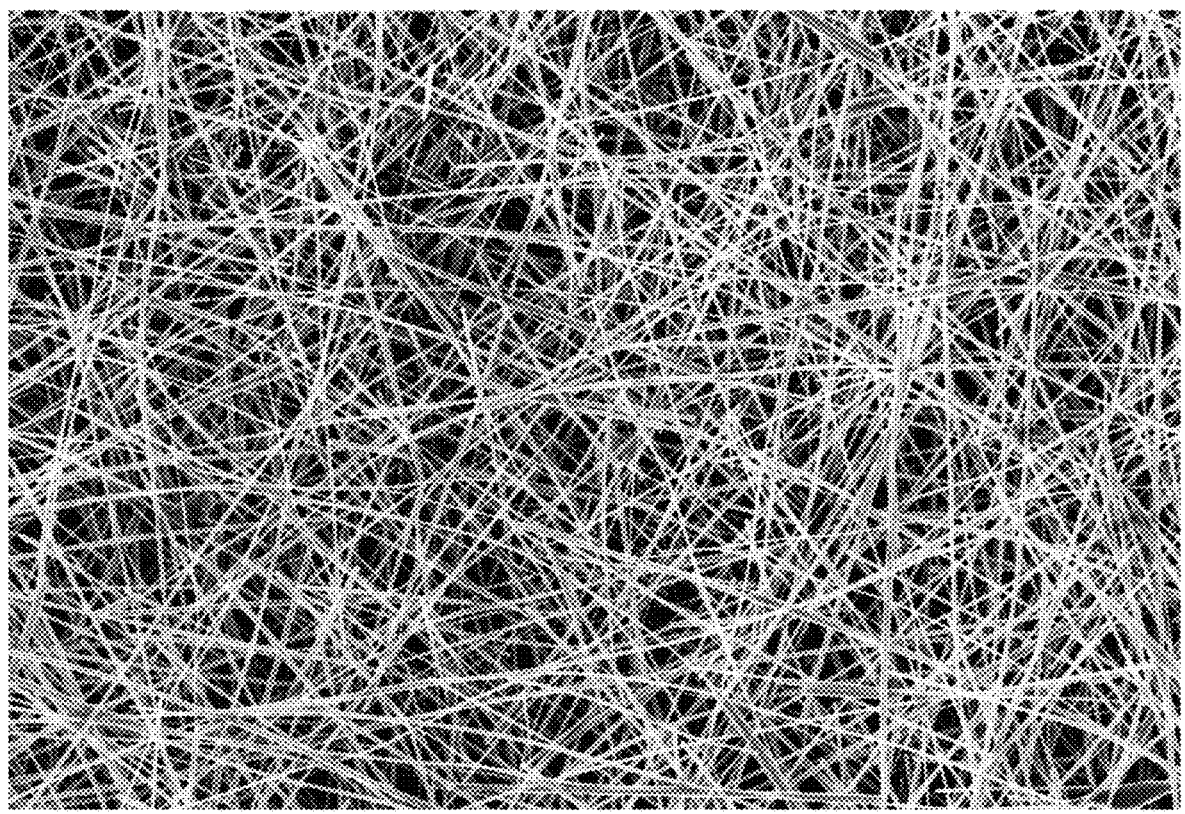
FIGS. 5A and 5B are conceptual images illustrating an example of electrically conductive nanomaterials that may be used as an antenna of this disclosure.
Figure 5B:
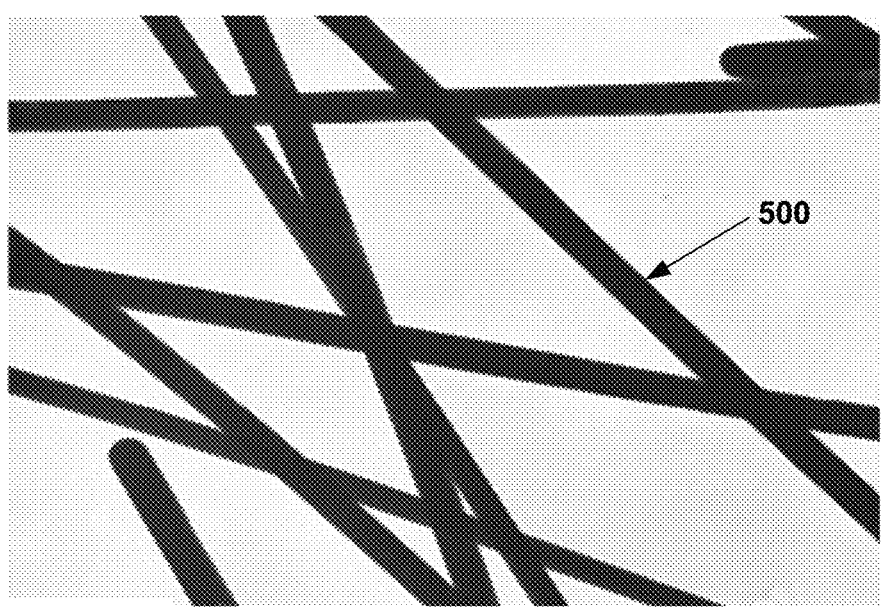

FIGS. 5A and 5B are conceptual images illustrating an example of electrically conductive nanostructures that may be used as an antenna of this disclosure. FIG. 5B illustrates a zoomed in view of the electrically conductive nanostructures, e.g., a nanowire network of FIG. 5A. In the example of silver nanowires, a square foot of silver nanowires dispersed on a substrate may include approximately fifteen kilometers of nanowire. Wire 500 in FIG. 5B may have a diameter in the tens of nanometers (nm). In some examples, an RF harvesting antenna of this disclosure may include a network of nanowires, such as that depicted by FIG. 5A. An RF harvesting antenna implemented using a material like a silver nano-wire matrix, copper nano-materials, carbon nanotubes, graphene or other materials with similar characteristics result in significantly more energy transfer, when compared to other types of antennae. In some examples, the use of more edges, e.g., receiving legs of various lengths, may enhance the performance of the antenna. A nanowire matrix, with a very large number of edges and high conductivity when compared to other materials may enhance the performance of the antenna. In some examples, the nanowire matrix may comprise nanowires of a variety of lengths to implement a broad band antenna. In other examples, the variety of lengths may implement an RF harvesting antenna that targets selected specific frequency ranges, e.g., the MICS frequency band, frequencies less than 20 MHz and similar frequency bands.

In some examples, a nanowire antenna may be arranged as a random laydown as shown FIGS. 5A and 5B. In other examples, not shown in FIGS. 5A and 5B a nanowire-based antenna may be used to form a shaped antenna, e.g., fractal geometry, dipole, or other geometry where the nanowires provide additional complexity to the shape desired.

Other materials to implement an RF harvesting antenna (not shown in FIGS. 5A and 5B) may include flexible printed circuit boards (PCB) printed with copper, titanium, silver, gold, or similar materials, with different trace lengths, shapes, and patterns. Another example may include indium tin oxide (ITO) deposited on a substrate in various trace lengths, shapes, and patterns. An RF harvesting antenna may also be implemented using a graphene hexagonal lattice deposited on a substrate. In other examples, antennae may be implemented using metamaterials (MTM), e.g., a synthetic composite material with a structure such that the material may exhibits properties not usually found in natural materials. In some examples, the antenna may be patterned by various techniques including 3D printing, photolithography, pulsed laser patterning, or micro dispense printing. In instances where nanomaterials are used in the antennae, a protective coating may prevent the nanomaterials from becoming toxic in the human body. Protective coatings may be polymeric in nature such as parylene, silicone, polyester, polysulfone, polycarbonate, or the like, as described above in relation to FIG. 3B.

As described above in relation to FIG. 4A, in some examples an antenna may be implemented on multiple planes. In some examples, different types of antenna may be included on different planes of the same antenna structure. For example, a fractal antenna element may be printed or placed on a first layer. A nanowire-based antenna element may be printed or placed on a second layer different from the first layer. A third type of antenna may be printed on a third layer, and so on. In this manner, a single antenna structure may be configured to harvest two or more frequency bands based on the arrangement of the layers. In some examples each layer is approximately parallel to the other layers. In other words, a first plane defined by an X-axis and a Y-axis containing a first antenna element is approximately parallel to a second plane defined by a second X-axis and Y-axis containing a second antenna element. Each antenna element may be separated and electrically isolated from each other by, for example, a third plane of a dielectric or other insulative material. In this disclosure, "approximately parallel" means the layers are parallel within manufacturing and measurement tolerances. The layers may be considered parallel even with some slight variation from perfectly parallel, e.g., cause by texture.

In other examples, an antenna may be arranged as a three-dimensional (3D) antenna. The arrangement of multiple antennae depicted in FIG. 3A may be considered a 3D antenna. In other examples, a 3D antenna may be arranged, for example, as an electrical lens (not shown).

Figure 6:
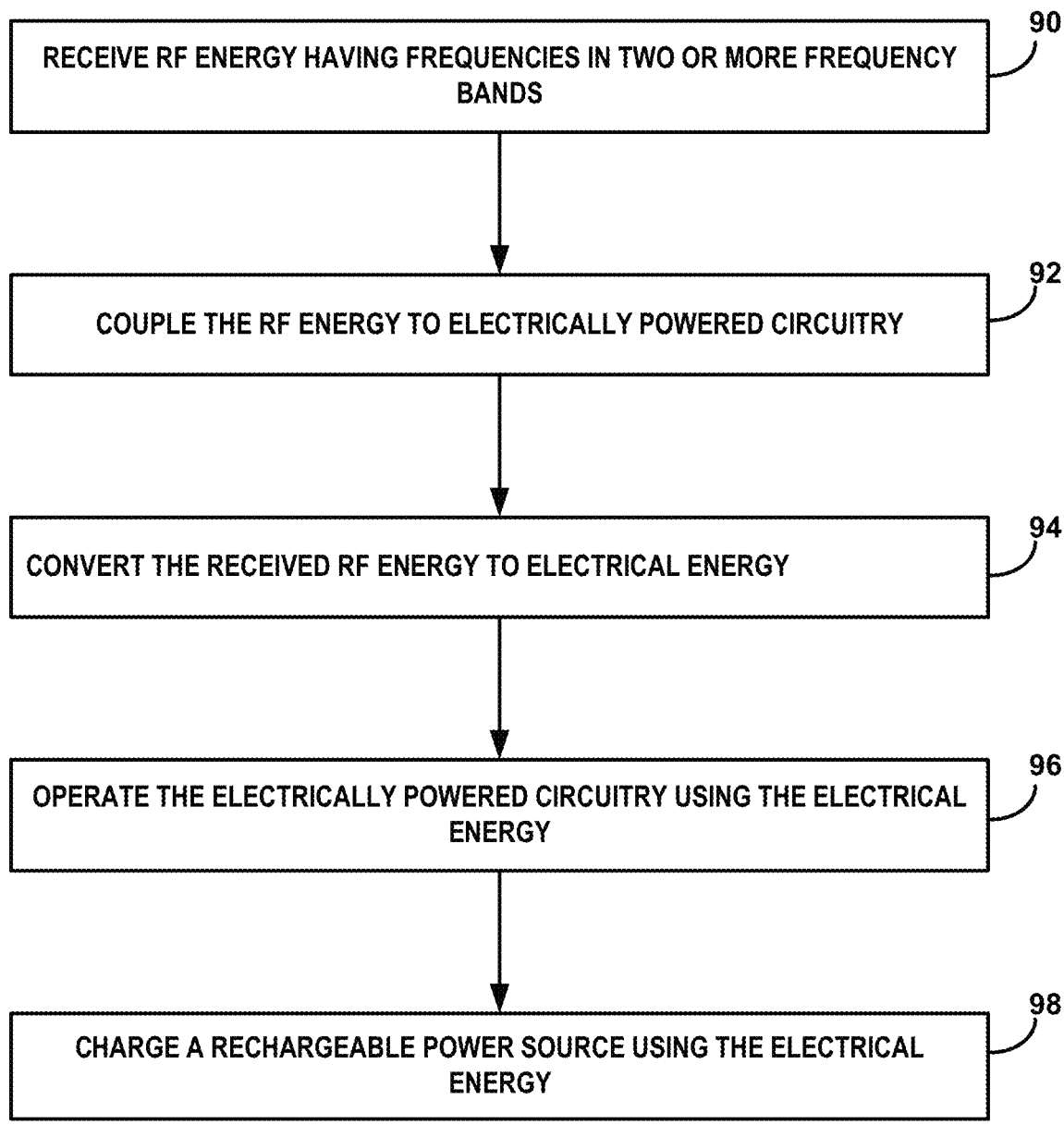
FIG. 6 is a flowchart illustrating an example operation of the RF harvesting techniques of this disclosure. The blocks of FIG. 6 will be described in terms of FIG. 2, unless otherwise noted.

FIG. 6 is a flowchart illustrating an example operation of the RF harvesting techniques of this disclosure. The blocks of FIG. 6 will be described in terms of FIG. 2, unless otherwise noted.

A first portion of an antenna, such as the dipole portions of antennae 72 may receive RF energy from the environment surrounding a device having electrical circuitry, such as IMD 16 (90). In some examples, the RF energy may have frequencies in two or more frequency bands, e.g., UHF band, MICS band and so on. In some examples the frequency bands may overlap.

A second portion of the antenna, e.g., conductors such as 74 and 76 may couple the RF energy to the electrically powered circuitry of the device (92). In some examples conductors 74 and 76 may pass through a hermetically sealed structure from outside a housing of a device to reach the electrical circuitry.

Circuitry within the device, such as charging circuitry 66 may convert the received RF energy to electrical energy (94). In some examples the converted electrical energy may be used directly to operate the electrically powered circuitry (96). In other examples, charging circuity 66 may direct the electrical energy to charge a rechargeable power source, such as power source 58.

In one or more examples, the functions described above may be implemented in hardware, software, firmware, or any combination thereof. For example, the various components of FIG. 2, such as processing circuitry 50, may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium. The term "non-transitory" may indicate that the storage medium is not embodied in a carrier wave or a propagated signal. In certain examples, a non-transitory storage medium may store data that can, over time, change (e.g., in RAM or cache).

By way of example, and not limitation, such computer-readable storage media, may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry. Accordingly, the term "processor," as used herein, may refer to any of the foregoing structure or any other structure suitable for implementation of the techniques described herein. Also, the techniques could be fully implemented in one or more circuits or logic elements.

The techniques of this disclosure may be implemented in a wide variety of devices or apparatuses, including, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Other details of this disclosure may be found in the following examples:

EXAMPLE 1

A wireless power receiving antenna comprising a first portion configured to wirelessly receive radio frequency (RF) energy having frequencies in two or more frequency bands; and a second portion configured to operatively couple the first portion to electrically powered circuitry and provide the received RF energy to operate the electrically powered circuitry, wherein the antenna is configured to be mounted to a case containing the electrically powered circuitry, and wherein: the case defines a first area, and the antenna defines a second area smaller than the first area.

EXAMPLE 2

The antenna of example 1, wherein the two or more frequency bands comprise: a first frequency band of 10 MHz-20 MHz, and a second frequency band of 100 MHz-700 MHz.

EXAMPLE 3

The antenna of any combination of examples 1 and 2, wherein the two or more frequency bands comprise a Medical Implant Communication Service (MICS) frequency band.

EXAMPLE 4

The antenna of any combination of examples 1 through 3, wherein a geometry of the antenna comprises a fractal geometry.

EXAMPLE 5

The antenna of any combination of examples 1 through 4, wherein the geometry of the antenna is based on a Koch snowflake geometry.

EXAMPLE 7

The antenna of any combination of examples 1 through 5, wherein a first element of the antenna is on a first layer and a second element of the antenna is on a second layer electrically isolated from the first layer, and wherein the first layer is approximately parallel to the second layer.

EXAMPLE 8

The antenna of any combination of examples 1 through 7, wherein the first element comprises a fractal geometry and the second element comprises a geometry different from the first element.

EXAMPLE 9

The antenna of any of examples 1 through 7, wherein the antenna is a first antenna mounted on a first side of the case, and wherein a second antenna is mounted on a second side of the case different from the first side.

EXAMPLE 10

The antenna of any combination of examples 1 through 8, wherein the antenna is constructed as a heat pipe and wherein the antenna is further configured to transfer heat from a first segment of the antenna to a second segment of the antenna.

EXAMPLE 11

The antenna of any combination of examples 1 through 9, wherein the antenna is printed to a substrate, and the substrate is mounted on the case.

EXAMPLE 12

A wireless power receiving antenna comprising a first portion configured to wirelessly receive radio frequency (RF) energy having frequencies in two or more frequency bands, wherein the two or more frequency bands comprise: a first frequency band of 10-20 MHz, and a second frequency band of 100-700 MHz; and a second portion configured to operatively couple the first portion to an electrically powered device and provide the received RF energy to operate the electrically powered device.

EXAMPLE 13

The antenna of example 12, wherein the antenna is separate from a case containing the electrically powered device.

EXAMPLE 14

The antenna of any combination of examples 12 through 13, wherein the antenna is a fractal antenna, encased in a non-conductive sealed housing.

EXAMPLE 15

The antenna of any combination of examples 12 through 13, wherein the antenna comprises electrically conductive nanostructures.

EXAMPLE 16

The antenna of any combination of examples 12 through 14, wherein the antenna comprises an antenna element that forms a shielding for an implantable medical device lead.

EXAMPLE 17

The antenna of any combination of examples 12 through 15, wherein the antenna comprises an antenna element that also acts as a conductor for an electrode of an implantable medical device lead.

EXAMPLE 18

The antenna of any combination of examples 12 through 16, wherein the two or more frequency bands comprise the Medical Implant Communication Service (MICS) frequency band.

EXAMPLE 19

The antenna of any combination of examples 12 through 17, wherein the antenna is configured to be implanted in live tissue and receive RF energy that has been refracted and changed by the tissue.

EXAMPLE 20

A method for receiving RF energy includes receiving, by a first portion of an antenna, radio frequency (RF) energy having frequencies in two or more frequency bands, coupling, by a second portion of the antenna, the RF energy to electrically powered circuitry; converting the received RF energy to electrical energy; operating the electrically powered circuitry using the electrical energy; and charging a rechargeable power source using the electrical energy, wherein the antenna is configured to be mounted on a case containing the electrically powered circuitry, and wherein: the case defines a first area, and the antenna defines a second area smaller than the first area.

EXAMPLE 21

The method of example 20, wherein the two or more frequency bands comprise: a first frequency band of 10-20 MHz, and a second frequency band of 100-700 MHz.

EXAMPLE 22

The method of any combination of examples 20 and 21, wherein the two or more frequency bands comprise a Medical Implant Communication Service (MICS) frequency band.

EXAMPLE 23

The method of any combination of examples 20 through 22, wherein a geometry of the antenna comprises a fractal geometry.

EXAMPLE 24

The method of any combination of examples 20 through 23, wherein the geometry of the antenna is based on a Koch snowflake geometry.

EXAMPLE 25

The method of any combination of examples 20 through 24, wherein the antenna comprises electrically conductive nanostructures.

EXAMPLE 26

The method of any combination of examples 20 through 25, wherein a first element of the antenna is on a first layer and a second element of the antenna is on a second layer electrically isolated from the first layer, and wherein the first layer is approximately parallel to the second layer.

EXAMPLE 27

The method of any combination of examples 20 through 26, wherein the first element comprises a fractal geometry and the second element comprises a geometry different from the first element.

EXAMPLE 28

A method for receiving RF energy comprising receiving, by a first portion of an antenna, radio frequency (RF) energy having frequencies in two or more frequency bands, wherein the two or more frequency bands comprise: a first frequency band of 10-20 MHz, and a second frequency band of 100-700 MHz; coupling, by a second portion of the antenna, the RF energy to electrically powered circuitry; converting the received RF energy to electrical energy; operating the electrically powered circuitry using the electrical energy; and charging a rechargeable power source using the electrical energy.

EXAMPLE 29

The method of example 28, wherein the antenna is separate from a case containing the electrically powered circuitry.

EXAMPLE 30

The method of examples 28 and 29, wherein the antenna is a fractal antenna, encased in a non-conductive sealed housing.

EXAMPLE 31

The method of any combination of examples 28 through 30, wherein the antenna comprises electrically conductive nanostructures.

EXAMPLE 32

The method of any combination of examples 28 through 31, wherein the antenna comprises an antenna element that forms a shielding for an implantable medical device lead.

EXAMPLE 33

The method of any combination of examples 28 through 32, wherein the antenna comprises an antenna element that also acts as a conductor for an electrode of an implantable medical device lead.

EXAMPLE 34

The method of any combination of examples 28 through 33, wherein the two or more frequency bands comprise a Medical Implant Communication Service (MICS) frequency band.

EXAMPLE 35

A system comprising an implantable medical device; and wireless power receiving antenna includes a first portion configured to wirelessly receive radio frequency (RF) energy having frequencies in two or more frequency bands, wherein the two or more frequency bands comprise: a first frequency band of 10-20 MHz, and a second frequency band of 100-700 MHz; and a second portion configured to operatively couple the first portion to an electrically powered device and provide the received RF energy to operate the electrically powered device.

EXAMPLE 36

The system of example 35, wherein the antenna is a first antenna, the system further includes a first portion of the second antenna configured to wirelessly receive radio frequency (RF) energy having frequencies in two or more frequency bands; and a second portion of the second antenna configured to operatively couple the first portion to electrically powered circuitry and provide the received RF energy to operate the electrically powered circuitry, wherein the first antenna and the second antenna are configured to be mounted on a case containing the electrically powered device, and wherein: the case defines a first area, the first antenna defines a second area smaller than the first area and the second antenna defines a third area smaller than the first area.

EXAMPLE 37

A system comprising an implantable medical device includes mounted on the housing, configured to transfer heat from a first region of the at least two regions to a second region of the at least two regions.

EXAMPLE 38

The system of example 37, wherein the passive heat transfer device comprises a vacuum chamber external to the housing, and wherein the vacuum chamber contains a working fluid.

EXAMPLE 39

The system of examples 37 and 38, wherein the passive heat transfer device comprises a heat pipe containing a working fluid.

EXAMPLE 40

The system of any combination of examples 37 through 39, wherein the heat pipe forms the shape of a wireless power receiving antenna includes a first portion configured to wirelessly receive radio frequency (RF) energy having frequencies in two or more frequency bands; and a second portion configured to operatively couple the first portion to electrically powered circuitry and provide the received RF energy to operate the electrically powered circuitry, wherein: the housing of the implantable medical device contains the electrically powered circuitry, the case defines a first area, and the antenna defines a second area smaller than the first area.

EXAMPLE 41

A system comprising an implantable medical device; and wireless power receiving antenna includes a first portion printed on a substrate, and configured to wirelessly receive radio frequency (RF) energy having frequencies in two or more frequency bands, wherein the two or more frequency bands comprise: a first frequency band of 10-20 MHz, and a second frequency band of 100-700 MHz; and a second portion configured to operatively couple the first portion to an electrically powered device and provide the received RF energy to operate the electrically powered device.

EXAMPLE 42

The system of example 41, wherein the implantable medical device comprises a housing, and wherein the housing comprises the substrate.

EXAMPLE 43

The system of example 41, wherein the two or more frequency bands further comprise a frequency band that includes 2.4 GHz.

Various examples of the disclosure have been described. These and other examples are within the scope of the following claims.

What is claimed is:

1. An implantable wireless power receiving antenna, the antenna comprising:
a first portion configured to wirelessly receive radio frequency (RF) energy having frequencies in two or more frequency bands; and
a second portion configured to operatively couple the first portion to electrically powered circuitry and provide the received RF energy to operate the electrically powered circuitry,
wherein the electrically powered circuitry is enclosed in a case for an implantable medical device, the case configured to contain and hermetically seal the electrically powered circuitry,
wherein the antenna is constructed as a heat pipe, and
wherein the antenna is further configured to transfer heat from a first segment of the antenna to a second segment of the antenna.

2. The antenna of claim 1, wherein the two or more frequency bands comprise:
a first frequency band of 10 MHz-20 MHz, and
a second frequency band of 100 MHz-700 MHz.

3. The antenna of claim 1, wherein the two or more frequency bands comprise a Medical Implant Communication Service (MICS) frequency band.

4. The antenna of claim 1, wherein a geometry of the antenna comprises a fractal geometry.

5. The antenna of claim 4, wherein the geometry of the antenna is based on a Koch snowflake geometry.

6. The antenna of any claim 1,
wherein the antenna comprises electrically conductive nanostructures comprising a network of nanowires, and
wherein the nanowires are of multiple lengths, wherein each length targets the RF energy in the two or more frequency bands.

7. The antenna of claim 1,
wherein the first portion of the antenna is implanted at a first location on a patient, and operatively coupled to the case, which is implanted at a second location on the patient separate from the first location.

8. The antenna of claim 1,
wherein the antenna is a first antenna mounted on a first side of the case, and
wherein a second antenna is mounted on a second side of the case different from the first side, wherein the second antenna:
is operatively coupled to the electrically powered circuitry and
also provides the received RF energy to operate the electrically powered circuitry.

9. The antenna of claim 1, wherein the first portion is mounted on the case containing the electrically powered circuitry.

10. The antenna of claim 9, wherein the antenna is printed to a substrate, and the substrate is mounted on the case.

11. A method for receiving RF energy, the method comprising:
receiving, by a first portion of an antenna implanted in tissue of a patient, radio frequency (RF) energy, the antenna configured to harvest energy from frequencies in the two frequency bands of:
a first frequency band of 10-20 MHz, and
a second frequency band of 100-700 MHz;
coupling, by a second portion of the antenna, the RF energy to electrically powered circuitry;
converting the received RF energy to electrical energy;
operating the electrically powered circuitry using the electrical energy; and
charging a rechargeable power source using the electrical energy,
wherein the antenna is mounted on a hermetically sealed, implantable case containing the electrically powered circuitry,
wherein the antenna is constructed as a heat pipe and wherein:
the case defines a first area, and
the antenna defines a second area smaller than the first area.

12. The method of claim 11,
wherein the antenna is further configured to transfer heat from a first segment of the antenna to a second segment of the antenna.

13. The method of claim 11, wherein a geometry of the antenna comprises a fractal geometry.

14. The method of claim 11, wherein the geometry of the antenna is based on a Koch snowflake geometry.

15. The method of claim 11, wherein the antenna comprises nanowires.

16. The method of claim 11,
wherein a first element of the antenna is on a first layer and a second element of the antenna is on a second layer electrically isolated from the first layer, and
wherein the first layer is approximately parallel to the second layer.

17. The method of claim 11, wherein the first element comprises a fractal geometry and the second element comprises a geometry different from the first element.

18. A system comprising:
an implantable medical device comprising electrically powered circuitry and a case configured to contain and hermetically seal the electrically powered circuitry; and
a wireless power receiving antenna, the antenna comprising:
a first portion configured to wirelessly harvest radio frequency (RF) energy having frequencies in one or both of the two frequency bands of:
a first frequency band of 10-20 MHz, and
a second frequency band of 100-700 MHz; and
a second portion configured to operatively couple the first portion to the electrically powered circuitry of the implantable medical device and provide the received RF energy to operate the electrically powered circuitry, wherein the antenna is constructed as a heat pipe.

19. The system of claim 18, wherein the antenna is a first antenna, the system further comprising a second antenna including:
- a first portion of the second antenna configured to wirelessly receive the RF energy; and
- a second portion of the second antenna configured to operatively couple the first portion of the to the electrically powered circuitry and also provide the received RF energy to operate the electrically powered circuitry,
- wherein the first antenna and the second antenna are mounted on the case containing the electrically powered circuitry, and wherein:
  - the first antenna is mounted on a first side of the case, and
  - the second antenna is mounted on a second side of the case opposite the first side.

20. The system of claim 18, wherein, a geometry of the antenna comprises a fractal geometry.

\* \* \* \* \*